US012774479B2

(12) United States Patent
Maeda et al.

(10) Patent No.: US 12,774,479 B2
(45) Date of Patent: Oct. 27, 2026

(54) FERMENTING ORGANISM FOR ETHANOL PRODUCTION

(71) Applicants: Novozymes A/S, Bagsvaerd (DK); Microbiogen Pty. Ltd., Sydney (AU)

(72) Inventors: Roberto Nobuyuki Maeda, Curitiba (BR); Philip John Livingstone Bell, Turramurra (AU)

(73) Assignees: Novozymes A/S, Bagsvaerd (DK); Microbiogen Pty. Ltd., Sydney (AU)

( * ) Notice: Subject to any disclaimer, the term of this patent is extended or adjusted under 35 U.S.C. 154(b) by 652 days.

(21) Appl. No.: 18/043,978

(22) PCT Filed: Sep. 3, 2021

(86) PCT No.: PCT/EP2021/074372
§ 371 (c)(1),
(2) Date: Mar. 3, 2023

(87) PCT Pub. No.: WO2022/049250
PCT Pub. Date: Mar. 10, 2022

(65) Prior Publication Data

US 2023/0332188 A1 Oct. 19, 2023

Related U.S. Application Data

(60) Provisional application No. 63/074,709, filed on Sep. 4, 2020, provisional application No. 63/157,551, filed on Mar. 5, 2021.

(51) Int. Cl.

| | |
|---|---|
| ***C12P 7/10*** | (2006.01) |
| ***C12N 1/185*** | (2026.01) |
| ***C12N 9/10*** | (2006.01) |
| ***C12N 9/12*** | (2006.01) |
| ***C12N 9/90*** | (2006.01) |
| ***C12N 15/81*** | (2006.01) |
| ***C12R 1/865*** | (2006.01) |

(52) U.S. Cl.
CPC ................ *C12P 7/10* (2013.01); *C12N 1/185* (2021.05); *C12N 9/1022* (2013.01); *C12N 9/1205* (2013.01); *C12N 9/90* (2013.01); *C12N 15/81* (2013.01); *C12R 2001/865* (2021.05); *C12Y 202/01001* (2013.01); *C12Y 202/01002* (2013.01); *C12Y 207/01017* (2013.01); *C12Y 501/03001* (2013.01); *C12Y 503/01005* (2013.01); *C12Y 503/01006* (2013.01); *C12Y 503/02005* (2015.07)

(58) Field of Classification Search
None
See application file for complete search history.

(56) References Cited

U.S. PATENT DOCUMENTS

| | | | | |
|---|---|---|---|---|
| 8,586,336 | B2 | 11/2013 | Bao et al. | |
| 10,889,836 | B2 * | 1/2021 | Yazdi | C12P 7/06 |
| 11,473,109 | B2 * | 10/2022 | Attfield | C12N 1/185 |
| 2006/0216804 | A1 * | 9/2006 | Karhumaa | C12N 15/52 435/254.21 |
| 2010/0035306 | A1 * | 2/2010 | Op Den Camp | C12N 9/1205 435/254.6 |
| 2020/0157581 | A1 | 5/2020 | Hogsett et al. | |

FOREIGN PATENT DOCUMENTS

| | | | |
|---|---|---|---|
| WO | 2003062430 | A1 | 7/2003 |
| WO | 2016045569 | A1 | 3/2016 |

OTHER PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*

* cited by examiner

*Primary Examiner* — Christian L Fronda
(74) *Attorney, Agent, or Firm* — Eric J. Fechter

(57) ABSTRACT

The present invention relates to processes for producing ethanol comprising saccharifying cellulosic or starch-containing material and fermenting the saccharified material with a fermenting microorganism to produce ethanol. The fermenting organism is *Saccharomyces cerevisiae* strain MBG5151 (deposited under Accession No. Y-67971 at the Agricultural Research Service Culture Collection (NRRL), Illinois 61604 U.S.A.), *Saccharomyces cerevisiae* strain MBG5248 (deposited under Accession No. Y-68015 at the Agricultural Research Service Culture Collection (NRRL), Illinois 61604 U.S.A.) or a fermenting organism that has properties that the same or about the same as that of *Saccharomyces cerevisiae* MBG5151 or MBG5248.

20 Claims, 8 Drawing Sheets

FERMENTING ORGANISM FOR ETHANOL PRODUCTION

CROSS-REFERENCE TO RELATED APPLICATIONS

This application is a 35 U.S.C. 371 national application of PCT/EP2021/074372, filed Sep. 3, 2021, which claims priority or the benefit from U.S. Provisional Application Ser. No. 63/074,709, filed Sep. 4, 2020, and U.S. Provisional Application Ser. No. 63/157,551 filed Mar. 5, 2021. The contents of these applications are fully incorporated herein by reference.

REFERENCE TO A DEPOSIT OF BIOLOGICAL MATERIAL

This application contains a reference to a deposit of biological material, which is incorporated herein by reference.

BACKGROUND

Ethanol is a transportation fuel commonly blending into gasoline. Cellulosic material is used as a feedstock in ethanol production processes. There are several processes in the art for making cellulose and hemicelluloses hydrolysates containing glucose, mannose, xylose and arabinose. Glucose and mannose are efficiently converted to ethanol during natural anaerobic metabolism. By far the most efficient ethanol producing microorganism is the yeast *Saccharomyces cerevisiae*. However, *Saccharomyces cerevisiae* lacks the necessary enzymes to convert the dominant sugar xylose into xylulose and is therefore unable to utilize xylose as a carbon source. To do so requires genetic engineering of *Saccharomyces cerevisiae* to express enzymes that can convert xylose into xylulose. One of the enzymes needed is xylose isomerase (E.C. 5.3.1.5) which converts xylose into xylulose, which can then be converted into ethanol during fermentation by *Saccharomyces cerevisiae.*

WO2003/062430 discloses that the introduction of a functional *Piromyces* xylose isomerase (XI) into *Saccharomyces cerevisiae* allows slow metabolism of xylose via the endogenous xylulokinase (EC 2.7.1.17) encoded by XKS1 and the enzymes of the non-oxidative part of the pentose phosphate pathway and confers to the yeast transformants the ability to grow on xylose.

U.S. Pat. No. 8,586,336 disclosed a *Saccharomyces cerevisiae* yeast strain expressing a xylose isomerase obtained by bovine rumen fluid. The yeast strain can be used to produce ethanol by culturing under anaerobic fermentation conditions. WO2016/045569 describes *Saccharomyces cerevisiae* strain CIBTS1260 with improved xylose consumption, glucose consumption, and ethanol production.

Despite significant improvement of ethanol production processes from cellulosic material, there is still a desire and need for providing improved processes, in particular, for improved fermentation kinetics which is beneficial to improve robustness to fermentation inhibitors.

SUMMARY

Described herein are, inter alia, processes for producing ethanol from cellulosic-containing or starch-containing material and suitable yeasts for use in such processes.

A first aspect relates to a method of producing a fermentation product from a cellulosic-containing and/or starch-containing material, the method comprising:

(a) saccharifying the cellulosic-containing or starch-containing material; and (b) fermenting the saccharified material of step (a) with a fermenting organism under suitable conditions to produce the fermentation product; wherein the fermenting organism is a recombinant strain of *Saccharomyces cerevisiae* deposited under the Budapest Treaty at the Agricultural Research Service Patent Culture Collection (NRRL) having deposit accession no. NRRL Y-67971 (*Saccharomyces cerevisiae* strain MBG5151), NRRL Y-68015 (*Saccharomyces cerevisiae* strain MBG5248), or a derivative thereof (e.g., expressing a heterologous polypeptide such as a glucoamylase and/or alpha-amylase) or a fermenting organism having properties that are about the same as that of *Saccharomyces cerevisiae* MBG5151 or *Saccharomyces cerevisiae* strain MBG5248.

In one embodiment, the method comprises recovering the fermentation product from the fermentation (e.g., by distillation).

In one embodiment, fermentation and saccharification are performed simultaneously in a simultaneous saccharification and fermentation (SSF). In one embodiment, fermentation and saccharification are performed sequentially (SHF).

In one embodiment, the fermentation product is ethanol.

In one embodiment, step (a) comprises contacting the starch-containing and/or cellulosic-containing material with an enzyme composition.

In one embodiment, step (a) comprises saccharifying a cellulosic-containing material. In one embodiment, the cellulosic-containing material is pretreated. In one embodiment, the cellulosic-containing material comprises bagasse.

In one embodiment, step (a) comprises contacting the cellulosic-containing material with an enzyme composition, and wherein the enzyme composition comprises one or more enzymes selected from a cellulase, an AA9 polypeptide, a hemicellulase, a CIP, an esterase, an expansin, a ligninolytic enzyme, an oxidoreductase, a pectinase, a protease, and a swollenin. In one embodiment, the cellulase is one or more enzymes selected from an endoglucanase, a cellobiohydrolase, and a beta-glucosidase. In one embodiment, the hemicellulase is one or more enzymes selected a xylanase, an acetylxylan esterase, a feruloyl esterase, an arabinofuranosidase, a xylosidase, and a glucuronidase.

In one embodiment, the method results in at least 0.25% (e.g., 0.5%, 0.75%, 1.0%, 1.25%, 1.5%, 1.75%, 2%, 3% or 5%) yield of fermentation product.

In one embodiment, fermentation is conducted under low oxygen (e.g., anaerobic) conditions.

In one embodiment, the fermenting organism has one or more of the following properties:

higher ethanol fermentation kinetics compared to *Saccharomyces cerevisiae* CIBTS1260 (e.g., between 10 and 32 hours) at 1 g DWC/L, 32° C., pH 5.5 (as described in Example 7 herein);

higher xylose consumption compared to *Saccharomyces cerevisiae* CIBTS1260 after 48 hours fermentation at 1 g DWC/L, 35° C., pH 5.5 (as described in Example 3 herein);

higher glucose consumption compared to *Saccharomyces cerevisiae* CIBTS1260 after 48 hours fermentation at 1 g DWC/L, 35° C., pH 5.5 (as described in Example 3 herein).

A second aspect relates to a recombinant *Saccharomyces cerevisiae* strain deposited under the Budapest Treaty at the Agricultural Research Service Patent Culture Collection (NRRL) having deposit accession no. NRRL Y-67971 (*Saccharomyces cerevisiae* strain MBG5151), NRRL Y-68015 (*Saccharomyces cerevisiae* strain MBG5248), or a derivative thereof (e.g., expressing a heterologous polypeptide such as a glucoamylase and/or alpha-amylase) or a fermenting organism having properties that are about the same as that of *Saccharomyces cerevisiae* MBG5151 or *Saccharomyces cerevisiae* strain MBG5248. In one embodiment, the strain has one or more of the following properties:

- higher ethanol fermentation kinetics compared to *Saccharomyces cerevisiae* CIBTS1260 (e.g., between 10 and 32 hours) at 1 g DWC/L, 32° C., pH 5.5 (as described in the Example 7 herein);
- higher xylose consumption compared to *Saccharomyces cerevisiae* CIBTS1260 after 48 hours fermentation at 1 g DWC/L, 35° C., pH 5.5 (as described in Example 3 herein);
- higher glucose consumption compared to *Saccharomyces cerevisiae* CIBTS1260 after 48 hours fermentation at 1 g DWC/L, 35° C., pH 5.5 (as described in Example 3 herein).

In one embodiment, the strain is capable of higher ethanol yield compared to *Saccharomyces cerevisiae* CIBTS1260 at 1 g DWC/L, 32° C., pH 5.5 (as described in Example 7 herein) between 10 to 30 hours of fermentation.

In one embodiment, the strain is capable of greater than 95% xylose consumption by 48 hours fermentation under the process conditions of 1 g DCW/L, 35° C., pH 5.5 (as described in Example 3 herein).

In one embodiment, the strain is capable of greater than 95% glucose consumption by 24 hours fermentation under the process conditions of 1 g DCW/L, 35° C., pH 5.5 (as described in Example 3 herein).

In one embodiment, the strain is capable of providing more than 30 g/L ethanol, such as more than 40 g/L ethanol, such as more than 45 g/L ethanol, such as approximately 47 g/L ethanol after 48 hours fermentation under the process conditions of 1 g DCW/L, 35° C., pH 5.5 (as described in Example 3 of herein).

In one embodiment, the strain comprises a heterologous gene encoding a xylose isomerase. In one embodiment, the strain comprises a heterologous gene encoding a pentose transporter, such as a GFX gene, (e.g., GFX1 from *Candida intermedia*). In one embodiment, the strain comprises a heterologous gene encoding a xylulokinase (XKS) (e.g., a XKS from *Saccharomyces cerevisiae*). In one embodiment, the strain comprises a heterologous gene encoding a ribulose 5 phosphate 3-epimerase (RPE1) (e.g., a RPE1 from *Saccharomyces cerevisiae*). In one embodiment, the strain comprises a heterologous gene encoding a ribulose 5 phosphate isomerase (RKI1) (e.g., a RKI1 from *Saccharomyces cerevisiae*). In one embodiment, the strain comprises comprising a heterologous gene encoding a transketolase (TKL1) and a heterologous gene encoding a transaldolase (TAL1) (e.g., a TKL1 and TAL1 from *Saccharomyces cerevisiae*).

A third aspect relates to a method of producing a derivative of NRRL Y-67971 (*Saccharomyces cerevisiae* strain MBG5151), or NRRL Y-68015 (*Saccharomyces cerevisiae* strain MBG5248), comprising: (a) culturing a first yeast strain with a second yeast strain, wherein the second yeast strain is NRRL Y-67971 (*Saccharomyces cerevisiae* strain MBG5151), or NRRL Y-68015 (*Saccharomyces cerevisiae* strain MBG5248), or a derivative thereof, under conditions which permit combining of DNA between the first yeast strain and the second yeast strain; and (b) isolating hybrid strains; and (c) optionally repeating steps (a) and (b) using a hybrid strain isolated in step (b) as the first yeast strain and/or the second yeast strain.

A fourth aspect relates to method of producing a derivative of NRRL Y-67971 (*Saccharomyces cerevisiae* strain MBG5151) which exhibits the defining characteristics of *Saccharomyces cerevisiae* strain MBG5151, or NRRL Y-68015 (*Saccharomyces cerevisiae* strain MBG5248) which exhibits the defining characteristics of *Saccharomyces cerevisiae* strain MBG5248, comprising: (a) providing: (i) a first yeast strain; and (ii) a second yeast strain, wherein the second yeast strain is *Saccharomyces cerevisiae* strain MBG5151, *Saccharomyces cerevisiae* strain MBG5248, or a derivative thereof; (b) culturing the first yeast strain and the second yeast strain under conditions which permit combining of DNA between the first and second yeast strains; (c) screening or selecting for a derivative of *Saccharomyces cerevisiae* strain MBG5151 or *Saccharomyces cerevisiae* strain MBG5248.

In one embodiment, step (c) comprises screening or selecting for a hybrid strain which exhibits one or more defining characteristic of *Saccharomyces cerevisiae* strain MBG5151 or *Saccharomyces cerevisiae* strain MBG5248. In one embodiment, the method further comprises the step of: (d) repeating steps (a) and (b) with the screened or selected strain from step (c) as the first and/or second strain, until a derivative is obtained which exhibits the defining characteristics of *Saccharomyces cerevisiae* strain MBG5151 or *Saccharomyces cerevisiae* strain MBG5248.

In one embodiment, the culturing step (b) comprises: (i) sporulating the first yeast strain and the second yeast strain; (ii) hybridizing germinated spores produced by the first yeast strain with germinated spores produced by the second yeast strain.

A fifth aspect relates to method of producing a recombinant derivative of NRRL Y-67971 (*Saccharomyces cerevisiae* strain MBG5151) or NRRL Y-68015 (*Saccharomyces cerevisiae* strain MBG5248), the method comprising: (a) transforming *Saccharomyces cerevisiae* strain MBG5151 (or a derivative thereof) or *Saccharomyces cerevisiae* strain MBG5248 (or a derivative thereof) with one or more expression vectors (e.g., one or more expression vectors encoding a glucoamylase and/or an alpha-amylase); and (b) isolating the transformed strain.

A sixth aspect relates to *Saccharomyces cerevisiae* strain produced by any of the third, forth or fifth aspects.

A seventh aspect relates to method of producing ethanol, comprising incubating a *Saccharomyces cerevisiae* strain of the second or sixth aspect with a substrate comprising a fermentable sugar under conditions which permit fermentation of the fermentable sugar to produce ethanol.

An eighth aspect relates to composition comprising a *Saccharomyces cerevisiae* strain of any second or sixth aspects, and one or more naturally occurring and/or non-naturally occurring components.

In one embodiment, the components are selected from the group consisting of: surfactants, emulsifiers, gums, swelling agents, and antioxidants.

In one embodiment, the *Saccharomyces cerevisiae* strain is *Saccharomyces cerevisiae* strain MBG5151 (deposited under Accession No. NRRL Y-67971 at the Agricultural Research Service Patent Culture Collection (NRRL), Northern Regional Research Center, 1815 University Street, Peoria, IL, USA).

In one embodiment, the *Saccharomyces cerevisiae* strain is *Saccharomyces cerevisiae* strain MBG5248 (deposited under Accession No. NRRL Y-68015 at the Agricultural Research Service Patent Culture Collection (NRRL), Northern Regional Research Center, 1815 University Street, Peoria, IL, USA).

In one embodiment, the *Saccharomyces cerevisiae* strain is in a viable form, in particular in dry, cream or compressed form.

DEFINITIONS

Figure 1:
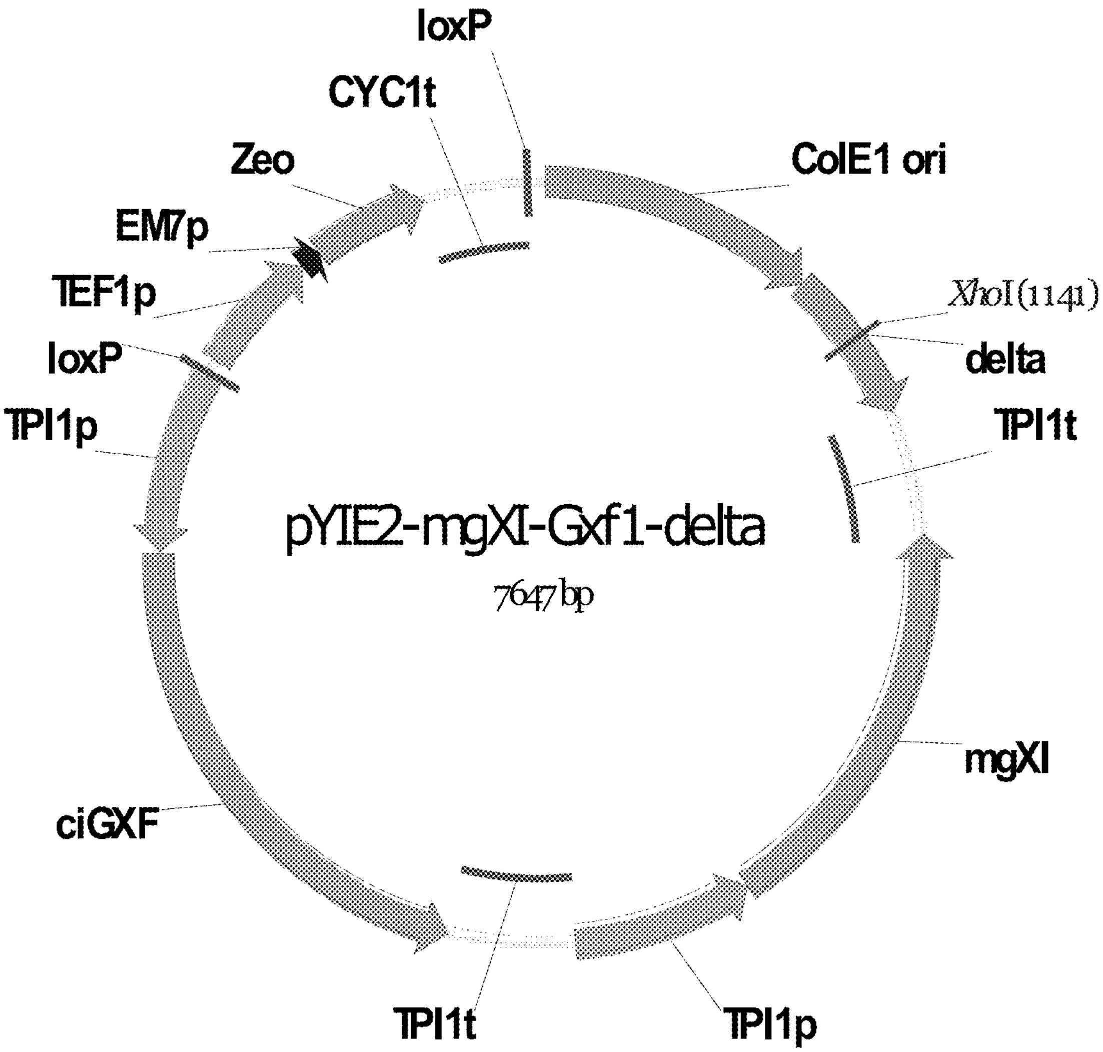
FIG. 1 shows a plasmid map of the plasmid pYIE2-mgXI-GXF1-delta harboring the mgXI and GXF expression cassettes.

Unless defined otherwise or clearly indicated by context, all technical and scientific terms used herein have the same meaning as commonly understood by one of ordinary skill in the art.

Allelic variant: The term “allelic variant” means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-amylase: The term “alpha amylase” means an 1,4-alpha-D-glucan glucanohydrolase, EC. 3.2.1.1, which catalyze hydrolysis of starch and other linear and branched 1,4-glucosidic oligo- and polysaccharides. Alpha-amylase activity can be determined using methods known in the art (e.g., using an alpha amylase assay described WO2020/023411).

Auxiliary Activity 9: The term “Auxiliary Activity 9” or “AA9” means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic-containing material by an enzyme having cellulolytic activity. Cellulolytic enhancing activity can be determined by measuring the increase in reducing sugars or the increase of the total of cellobiose and glucose from the hydrolysis of a cellulosic-containing material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40 C-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsværd, Denmark) and beta-glucosidase as the source of the cellulolytic activity, wherein the beta-glucosidase is present at a weight of at least 2-5% protein of the cellulase protein loading. In one embodiment, the beta-glucosidase is an *Aspergillus oryzae* beta-glucosidase (e.g., recombinantly produced in *Aspergillus oryzae* according to WO02/095014). In another embodiment, the beta-glucosidase is an *Aspergillus fumigatus* beta-glucosidase (e.g., recombinantly produced in *Aspergillus oryzae* as described in WO02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO2013/028928 for high temperature compositions.

AA9 polypeptides enhance the hydrolysis of a cellulosic-containing material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Beta-glucosidase: The term “beta-glucosidase” means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term “beta-xylosidase” means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Catalase: The term "catalase" means a hydrogen-peroxide:hydrogen-peroxide oxidoreductase (EC 1.11.1.6) that catalyzes the conversion of 2 $H_2O_2$ to $O_2$+2 $H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic-containing material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman N21 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic-containing material by cellulolytic enzyme(s) under the following conditions: 1-50 mg of cellulolytic enzyme protein/g of cellulose in pretreated corn stover (PCS) (or other pretreated cellulosic-containing material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, CA, USA).

Coding sequence: The term "coding sequence" or "coding region" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of the polypeptide including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Expression vector: The term "expression vector" means a linear or circular DNA molecule that comprises a polynucleotide encoding a polypeptide and is operably linked to control sequences that provide for its expression.

Fermentable medium: The term "fermentable medium" or "fermentation medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) by a host cell into a desired product, such as ethanol. In some instances, the fermentation medium is derived from a natural source, such as sugar cane, starch, or cellulose, and may be the result of pretreating the source by enzymatic hydrolysis (saccharification). The term fermentation medium is understood herein to refer to a medium before the fermenting organism is added, such as, a medium resulting from a saccharification process, as well as a medium used in a simultaneous saccharification and fermentation process (SSF).

Glucoamylase: The term "glucoamylase" (1,4-alpha-D-glucan glucohydrolase, EC 3.2.1.3) is defined as an enzyme that catalyzes the release of D-glucose from the non-reducing ends of starch or related oligo- and polysaccharide molecules. For purposes of the present invention, glucoamylase activity may be determined according to the procedures known in the art, such as those described in WO2020/023411.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Current Opinion In Microbiology 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Heterologous polynucleotide: The term "heterologous polynucleotide" is defined herein as a polynucleotide that is not native to the host cell; a native polynucleotide in which structural modifications have been made to the coding region; a native polynucleotide whose expression is quantitatively altered as a result of a manipulation of the DNA by recombinant DNA techniques, e.g., a different (foreign) promoter; or a native polynucleotide in a host cell having one or more extra copies of the polynucleotide to quantitatively alter expression. A "heterologous gene" is a gene comprising a heterologous polynucleotide.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" is defined herein as a polypeptide having biological activity that is in its final form following translation and any post-translational modifications, such as N-terminal processing, C-terminal truncation, glycosylation, phosphorylation, etc. The mature polypeptide sequence lacks a signal sequence, which may be determined using techniques known in the art (See, e.g., Zhang and Henzel, 2004, *Protein Science* 13: 2819-2824). The term "mature polypeptide coding sequence" means a polynucleotide that encodes a mature polypeptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Pentose: The term "pentose" means a five-carbon monosaccharide (e.g., xylose, arabinose, ribose, lyxose, ribulose, and xylulose). Pentoses, such as D-xylose and L-arabinose, may be derived, e.g., through saccharification of a plant cell wall polysaccharide.

Pretreated corn stover: The term "Pretreated Corn Stover" or "PCS" means a cellulosic-containing material derived from corn stover by treatment with heat and dilute sulfuric acid, alkaline pretreatment, neutral pretreatment, or any pretreatment known in the art.

Protease: The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in *Eur. J. Biochem.* 223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J. Biochem.* 264: 610-650 (1999); respectively. The term "subtilases" refer to a sub-group of serine protease according to Siezen et al., 1991, *Protein Engng.* 4: 719-737 and Siezen et al., 1997, *Protein Science* 6: 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Protease activity may be determined using methods described in the art (e.g., US 2015/0125925) or using commercially available assay kits (e.g., Sigma-Aldrich).

Pullulanase: The term "pullulanase" means a starch debranching enzyme having pullulan 6-glucano-hydrolase activity (EC 3.2.1.41) that catalyzes the hydrolysis the α-1,6-glycosidic bonds in pullulan, releasing maltotriose with reducing carbohydrate ends. For purposes of the present invention, pullulanase activity can be determined according to a PHADEBAS assay or the sweet potato starch assay described in WO2016/087237.

Sequence Identity: The relatedness between two amino acid sequences or between two nucleotide sequences is described by the parameter "sequence identity".

For purposes described herein, the degree of sequence identity between two amino acid sequences is determined using the Needleman-Wunsch algorithm (Needleman and Wunsch, *J. Mol. Biol.* 1970, 48, 443-453) as implemented in the Needle program of the EMBOSS package (EMBOSS: The European Molecular Biology Open Software Suite, Rice et al., *Trends Genet* 2000, 16, 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of the Referenced Sequence−Total Number of Gaps in Alignment)

For purposes described herein, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Referenced Sequence−Total Number of Gaps in Alignment)

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6.

Xylitol dehydrogenase: The term "xylitol dehydrogenase" or "XDH" (AKA D-xylulose reductase) is classified as E.C. 1.1.1.9 and means an enzyme that catalyzes the conversion of xylitol to D-xylulose. Xylitol dehydrogenase activity can be determined using methods known in the art (e.g., Richard et al., 1999, *FEBS Letters* 457, 135-138).

Xylose isomerase: The term "xylose isomerase" or "XI" means an enzyme which can catalyze D-xylose into D-xylulose in vivo, and convert D-glucose into D-fructose in vitro. Xylose isomerase is also known as "glucose isomerase" and is classified as E.C. 5.3.1.5. As the structure of the enzyme is very stable, the xylose isomerase is a good model for studying the relationships between protein structure and functions (Karimaki et al., Protein Eng Des Sel, 12004, 17 (12):861-869). Xylose Isomerase activity may be determined using techniques known in the art (e.g., a coupled enzyme assay using D-sorbitol dehygrogenase, as described by Verhoeven et. al., 2017, *Sci Rep* 7, 46155).

Xylulokinase: The term "xylulokinase" or "XK" is classified as E.C. 2.7.1.17 and means an enzyme that catalyzes the conversion of D-xylulose to D-xylulose 5-phosphate. Xylulokinase activity can be determined using methods known in the art (e.g., Richard et al., 2000, *FEBS Microbiol. Letters* 190, 39-43)

Reference to "about" a value or parameter herein includes embodiments that are directed to that value or parameter per se. For example, description referring to "about X" includes the embodiment "X". When used in combination with measured values, "about" includes a range that encompasses at least the uncertainty associated with the method of measuring the particular value, and can include a range of plus or minus two standard deviations around the stated value.

Likewise, reference to a gene or polypeptide that is "derived from" another gene or polypeptide X, includes the gene or polypeptide X.

As used herein and in the appended claims, the singular forms "a," "or," and "the" include plural referents unless the context clearly dictates otherwise.

It is understood that the embodiments described herein include "consisting" and/or "consisting essentially of" embodiments. As used herein, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

DETAILED DESCRIPTION

Described herein, inter alia, are recombinant fermenting organisms and methods for producing a fermentation product, such as ethanol, from cellulosic and/or starch containing material. The Applicant has created a new *Saccharomyces cerevisiae* strain with improved fermentation kinetics while maintaining fermentation yield. A strain having improved kinetics is desirable because, e.g., it may be more robust in the presence of inhibitors, advantageous for a variety of biomass pre-treatment conditions, and provide shorter fermentation times.

In one aspect is a method of producing a fermentation product from a cellulosic-containing or starch-containing material comprising:

(a) saccharifying the cellulosic-containing or starch-containing material; and (b) fermenting the saccharified material of step (a) with a recombinant fermenting organism described herein.

Steps a) and b) may be carried out either sequentially or simultaneously (SSF). In one embodiment, steps a) and b) are carried out simultaneously (SSF). In another embodiment, steps a) and b) are carried out sequentially.

Fermenting Organisms

In one embodiment, the fermenting organism is a recombinant strain of *Saccharomyces cerevisiae* deposited under the Budapest Treaty at the Agricultural Research Service Patent Culture Collection (NRRL) having deposit accession no. NRRL Y-67971 (*Saccharomyces cerevisiae* strain MBG5151), or a derivative thereof (e.g., expressing a heterologous polypeptide such as a glucoamylase and/or alpha-amylase) or a fermenting organism having properties that are about the same as that of *Saccharomyces cerevisiae* MBG5151.

The Applicant has produced strain NRRL Y-67971 (*Saccharomyces cerevisiae* strain MBG5151) from *Saccharomyces cerevisiae* CIBTS1260 (See, WO2016/045569, the content of which is incorporated here by reference) by evolution and breeding procedures described in U.S. Pat. No. 8,257,959. As shown in the Examples below, strain MBG5151 provides faster kinetics while maintaining similar ethanol titers when compared to CIBTS1260.

In another embodiment, the fermenting organism is a recombinant strain of *Saccharomyces cerevisiae* deposited under the Budapest Treaty at the Agricultural Research Service Patent Culture Collection (NRRL) having deposit accession no. NRRL Y-68015 (*Saccharomyces cerevisiae* strain MBG5248), or a derivative thereof (e.g., expressing a heterologous polypeptide such as a glucoamylase and/or alpha-amylase) or a fermenting organism having properties that are about the same as that of *Saccharomyces cerevisiae* MBG5248.

In one embodiment, the fermenting organism has one or more of the following properties:

- higher ethanol fermentation kinetics compared to *Saccharomyces cerevisiae* CIBTS1260 (e.g., between 10 and 32 hours) at 1 g DWC/L, 32° C., pH 5.5 (as described in Example 7 herein);
- higher xylose consumption compared to *Saccharomyces cerevisiae* CIBTS1260 after 48 hours fermentation at 1 g DWC/L, 35° C., pH 5.5 (as described in Example 3 herein);
- higher glucose consumption compared to *Saccharomyces cerevisiae* CIBTS1260 after 48 hours fermentation at 1 g DWC/L, 35° C., pH 5.5 (as described in Example 3 herein).

In one embodiment, the fermenting organism is capable of greater than 95% xylose consumption by 48 hours fermentation at 1 g DWC/L, 35° C., pH 5.5 (as described in Example 3 herein).

In one embodiment, the fermenting organism is capable of greater than 95% glucose consumption by 24 hours 24 hours fermentation at 1 g DWC/L, 35° C., pH 5.5 (as described in Example 3 herein).

In one embodiment, the fermenting organism is capable of higher yield of fermentation product (e.g., ethanol) compared to *Saccharomyces cerevisiae* CIBTS1260 under the same conditions (e.g., at 10, 15, 20, 25 or 30 hours of fermentation). In some embodiments, the fermenting organism is capable of at least 0.25%, such as 0.5%, 0.75%, 1.0%, 1.25%, 1.5%, 1.75%, 2%, 3% or 5% higher yield of the fermentation product (e.g., ethanol).

In one embodiment, the fermenting organism is capable of more than 30 g/L ethanol, such as more than 40 g/L ethanol, such as more than 45 g/L ethanol, such as more then 50 g/L ethanol after 48 hours fermentation at 1 g DWC/L, 35° C., pH 5.5 (as described in Example 3 or Example 7 herein).

In one embodiment, the fermenting organism is *Saccharomyces cerevisiae* MBG5151 (deposited under Accession No. NRRL Y-67971 at the Agricultural Research Service Culture Collection (NRRL), Illinois 61604 U.S.A.). In another embodiment, the fermenting organism is *Saccharomyces cerevisiae* MBG5248 (deposited under Accession No. NRRL Y-68015 at the Agricultural Research Service Culture Collection (NRRL), Illinois 61604 U.S.A.).

In one embodiment, the fermenting organism comprises a heterologous gene encoding a xylose isomerase (e.g., a xylose isomerase shown in SEQ ID NO: 13 of WO2016/045569, or an amino acid sequence having at least 80%, such as at least 90%, such as at least 95%, such as at least 96%, such as at least 97%, such as at least 98%, such as at least 99%, such as 100% sequence identity to SEQ ID NO: 13 of WO2016/045569).

In one embodiment, the fermenting organism comprises a heterologous gene encoding a pentose transporter, such as a GFX gene, in particular GFX1 from *Candida intermedia* (e.g., SEQ ID NO: 18 of WO2016/045569). In one embodiment, the pentose transporter gene has at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 18 of WO2016/045569.

In one embodiment, the fermenting organism comprises a heterologous (e.g., via overexpression) xylulokinase gene (XKS), such as an overexpressed XKS gene from *Saccharomyces cerevisiae.*

In one embodiment, the fermenting organism comprises a heterologous (e.g., via overexpression) ribulose 5 phosphate 3-epimerase gene (RPE1), such as an overexpressed RPE1 gene from *Saccharomyces cerevisiae.*

In one embodiment, the fermenting organism comprises a heterologous (e.g., via overexpression) ribulose 5 phosphate isomerase gene (RKI1), such as an overexpressed RKI1 gene from *Saccharomyces cerevisiae.*

In one embodiment, the fermenting organism comprises a heterologous (e.g., via overexpression) transketolase gene (TKL1) and transaldolase gene (TAL1), such as an overexpressed TKL1 gene and TAL1 gene from *Saccharomyces cerevisiae.*

In one embodiment, the fermenting organism has one or more, such as one, two, three, four, five or all, of the following genetic modifications:

- a heterologous xylose isomerases gene (Ru-XI) obtained from bovine rumen fluid, in particular the one shown in SEQ ID NO: 20 of WO2016/045569, encoding the xylose isomerase shown in SEQ ID NO: 13 of WO2016/045569;
- a heterologous pentose transporter gene (GXF1) from *Candida intermedia*, in particular the one shown in SEQ ID NO: 18 of WO2016/045569;
- a heterologous xylulokinase gene (XKS), in particular from a type strain of *Saccharomyces cerevisiae;*
- a heterologous ribulose 5 phosphate 3-epimerase gene (RPE1), in particular from a type strain of *Saccharomyces cerevisiae;*
- a heterologous ribulose 5 phosphate isomerase gene (RKI1), in particular from a type strain of *Saccharomyces cerevisiae;*
- a heterologous transketolase gene (TKL1) and a heterologous transaldolase gene (TAL1), in particular from a type strain of *Saccharomyces cerevisiae.*

For instance, in one embodiment, the fermenting organism of the invention has the following genetic modifications:

- a heterologous xylose isomerases gene (Ru-XI) obtained from bovine rumen fluid, in particular the one shown in SEQ ID NO: 20 of WO2016/045569, encoding the xylose isomerase shown in SEQ ID NO: 13 of WO2016/045569;
- a heterologous xylulokinase gene (XKS), in particular from a type strain of *Saccharomyces cerevisiae;*
- a heterologous ribulose 5 phosphate 3-epimerase gene (RPE1), in particular from a type strain of *Saccharomyces cerevisiae;*
- a heterologous ribulose 5 phosphate isomerase gene (RKI1), in particular from a type strain of *Saccharomyces cerevisiae;*
- a heterologous transketolase gene (TKL1) and transaldolase gene (TAL1), in particular from a type strain of *Saccharomyces cerevisiae.*

The fermenting organism may also be a derivative of *Saccharomyces cerevisiae* strain MBG5151 or MBG5248.

As used herein, a "derivative" of *Saccharomyces cerevisiae* strain MBG5151 or MBG5248 is a strain derived from said strain, such as through mutagenesis, recombinant DNA technology, mating, cell fusion, or cytoduction between yeast strains. The strain derived from *Saccharomyces cerevisiae* strain MBG5151 or MBG5248 may be a direct progeny (i.e. the product of a mating between *Saccharomyces cerevisiae* strain MBG5151 or MBG5248 and another strain or itself), or a distant progeny resulting from an initial mating between *Saccharomyces cerevisiae* strain MBG5151 or MBG5248 and another strain or itself, followed by a large number of subsequent matings.

In one embodiment, a derivative of *Saccharomyces cerevisiae* strain MBG5151 or MBG5248 is a hybrid strain produced by culturing a first yeast strain with *Saccharomyces cerevisiae* strain MBG5151 or MBG5248 under conditions which permit combining of DNA between the first yeast strain and *Saccharomyces cerevisiae* strain MBG5151 or MBG5248.

In one embodiment, the derivative of *Saccharomyces cerevisiae* strain MBG5151 or MBG5248 exhibits one or more defining characteristics of *Saccharomyces cerevisiae* strain MBG5151 or MBG5248. Derivatives of *Saccharomyces* which exhibit one or more defining characteristics of *Saccharomyces cerevisiae* strain MBG5151 or MBG5248 are produced using *Saccharomyces cerevisiae* strain MBG5151 or MBG5248. In this regard, *Saccharomyces cerevisiae* strain MBG5151 or MBG5248 forms the basis for preparing other strains having the defining characteristics of *Saccharomyces cerevisiae* strain MBG5151 or MBG5248. For example, strains of *Saccharomyces* which exhibit one or more defining characteristics of *Saccharomyces cerevisiae* strain MBG5151 or MBG5248 can be derived from *Saccharomyces cerevisiae* strain MBG5151 or MBG5248, using methods such as classical mating, cell fusion, or cytoduction between yeast strains, mutagenesis or recombinant DNA technology.

In one embodiment, a derivative of *Saccharomyces cerevisiae* strain MBG5151 exhibits one or more defining characteristics of *Saccharomyces cerevisiae* strain MBG5151 may be produced by:

(a) culturing a first yeast strain with a second yeast strain, wherein the second yeast strain is *Saccharomyces cerevisiae* strain MBG5151 (or a derivative of *Saccharomyces cerevisiae* strain MBG5151) under conditions which permit combining of DNA between the first yeast strain and the second yeast strain;

(b) screening or selecting for a derivative of *Saccharomyces cerevisiae* strain MBG5151, such as screening or selecting fora derivative with increased ethanol production in corn mash compared to the first strain;

(c) optionally repeating steps (a) and (b) with the screened or selected strain as the first yeast strain and/or the second yeast strain, until a derivative of *Saccharomyces cerevisiae* strain MBG5151 is obtained which exhibits one or more defining characteristics of *Saccharomyces cerevisiae* strain MBG5151.

In one embodiment, a derivative of *Saccharomyces cerevisiae* strain MBG5248 exhibits one or more defining characteristics of *Saccharomyces cerevisiae* strain MBG5248 may be produced by:

(a) culturing a first yeast strain with a second yeast strain, wherein the second yeast strain is *Saccharomyces cerevisiae* strain MBG5248 (or a derivative of *Saccharomyces cerevisiae* strain MBG5248) under conditions which permit combining of DNA between the first yeast strain and the second yeast strain;

(b) screening or selecting for a derivative of *Saccharomyces cerevisiae* strain MBG5248, such as screening or selecting for a derivative with increased ethanol production in corn mash compared to the first strain;

(c) optionally repeating steps (a) and (b) with the screened or selected strain as the first yeast strain and/or the second yeast strain, until a derivative of *Saccharomyces cerevisiae* strain MBG5248 is obtained which exhibits one or more defining characteristics of *Saccharomyces cerevisiae* strain MBG5248.

The first yeast strain may be any strain of yeast if the DNA of the strain can be combined with the second yeast strain using methods such as classical mating, cell fusion or cytoduction. Typically, the first yeast strain is a *Saccharomyces* strain. More typically, the first yeast strain is a *Saccharomyces cerevisiae* strain. *Saccharomyces cerevisiae* is as defined by Kurtzman (2003) FEMS Yeast Research vol 4 pp. 233-245. The first yeast strain may have desired properties which are sought to be combined with the defining characteristics of *Saccharomyces cerevisiae* strain MBG5151. The first yeast strain may be, for example, any *Saccharomyces cerevisiae* strain, such as for example ETHANOL REDO. It will also be appreciated that the first yeast strain may be *Saccharomyces cerevisiae* strain MBG5151 or MBG5248 (or a derivative of *Saccharomyces cerevisiae* strain MBG5151 or MBG5248).

The first and second yeast strains are cultured under conditions which permit combining of DNA between the yeast strains. As used herein, "combining of DNA" between yeast strains refers to combining of all or a part of the genome of the yeast strains. Combining of DNA between yeast strains may be by any method suitable for combining DNA of at least two yeast cells, and may include, for example, mating methods which comprise sporulation of the yeast strains to produce haploid cells and subsequent hybridising of compatible haploid cells; cytoduction; or cell fusion such as protoplast fusion.

In one embodiment, culturing the first yeast strain with the second yeast, under conditions which permit combining of DNA between the first yeast strain and the second yeast strain, comprises:

(i) sporulating the first yeast strain and the second yeast strain;

(ii) germinating and hybridizing spores produced by the first yeast strain with spores produced by the second yeast strain.

In one embodiment, the method of producing a derivative of *Saccharomyces cerevisiae* strain MBG5151 which exhibits one or more defining characteristics of *Saccharomyces cerevisiae* strain MBG5151, comprises:

(a) providing: (i) a first yeast strain; and (ii) a second yeast strain, wherein the second yeast strain is *Saccharomyces cerevisiae* strain MBG5151 (or a derivative of *Saccharomyces cerevisiae* strain MBG5151);

(b) sporulating the first yeast strain and the second yeast strain;

(c) germinating and hybridizing the spores of the first yeast strain with germinated spores of the second yeast strain;

(d) screening or selecting for a derivative of *Saccharomyces cerevisiae* strain MBG5151, such as screening or selecting fora derivative with increased ethanol production compared to the first strain, and/or higher ethanol yield from glucose during fermentation of corn mash than the first strain;

(e) optionally repeating steps (b) to (d) with the screened or selected strain as the first and/or second yeast strain.

In one embodiment, the method of producing a derivative of *Saccharomyces cerevisiae* strain MBG5151 which exhibits one or more defining characteristics of *Saccharomyces cerevisiae* strain MBG5248, comprises:

(a) providing: (i) a first yeast strain; and (ii) a second yeast strain, wherein the second yeast strain is *Saccharomyces cerevisiae* strain MBG5248 (or a derivative of *Saccharomyces cerevisiae* strain MBG5248);

(b) sporulating the first yeast strain and the second yeast strain;

(c) germinating and hybridizing the spores of the first yeast strain with germinated spores of the second yeast strain;

(d) screening or selecting for a derivative of *Saccharomyces cerevisiae* strain MBG5248, such as screening or selecting for a derivative with increased ethanol production compared to the first strain, and/or higher ethanol yield from glucose during fermentation of corn mash than the first strain;

(e) optionally repeating steps (b) to (d) with the screened or selected strain as the first and/or second yeast strain.

Methods for sporulating, germinating and hybridizing yeast strains, and in particular, *Saccharomyces* strains, are known in the art and are described in, for example, Ausubel, F. M. et al., (1997) Current Protocols in Molecular Biology, Volume 2, pages 13.2.1 to 13.2.5 (John Wiley & Sons Inc); Chapter 7, "Sporulation and Hybridisation of yeast" by R. R. Fowell, in "The Yeasts" vol 1, A. H. Rose and J. S. Harrison (Eds), 1969, Academic Press.

In one embodiment, the yeast strains may be cultured under conditions which permit cell fusion. Methods for the generation of intraspecific or interspecific hybrids using cell fusion techniques are described in, for example, Spencer et al. (1990) in, Yeast Technology, Spencer J F T and Spencer D M (Eds), Springer Verlag, New York.

In another embodiment, the yeast strains may be cultured under conditions which permit cytoduction. Methods for cytoduction are described in, for example, Inge-Vechymov et al. (1986) Genetika 22: 2625-2636; Johnston (1990) in, Yeast technology, Spencer J F T and Spencer D M (Eds), Springer Verlag, New York.

In one embodiment, screening or selecting for derivatives of *Saccharomyces cerevisiae* strain MBG5151 or MBG5248 comprises screening or selecting for a derivative with increased ethanol production compared to the first strain, and/or screening or selecting for a hybrid which has a higher ethanol yield, e.g., as described in WO2019/161227.

In one embodiment, a derivative of *Saccharomyces cerevisiae* strain MBG5151 or MBG5248 which exhibits one or more defining characteristics of *Saccharomyces cerevisiae* strain MBG5151 or MBG5248, respectively, may be a mutant of *Saccharomyces cerevisiae* strain MBG5151 or MBG5248. Methods for producing mutants of *Saccharomyces* yeast, and specifically mutants of *Saccharomyces cerevisiae*, are known in the art and described in, for example, Lawrence C. W. (1991) Methods in Enzymology, 194: 273-281.

In another embodiment, a derivative of *Saccharomyces cerevisiae* strain MBG5151 which exhibits one or more defining characteristics of *Saccharomyces cerevisiae* strain MBG5151 may be a recombinant derivative of *Saccharomyces cerevisiae* strain MBG5151. In another embodiment, a derivative of *Saccharomyces cerevisiae* strain MBG5248 which exhibits one or more defining characteristics of *Saccharomyces cerevisiae* strain MBG5248 may be a recombinant derivative of *Saccharomyces cerevisiae* strain MBG5248. A recombinant derivative of *Saccharomyces cerevisiae* strain MBG5151 or MBG5248 is a strain produced by introducing into *Saccharomyces cerevisiae* strain MBG5151 or MBG5248 a nucleic acid using recombinant DNA technology. Recombinant methods for the introduction of nucleic acid into *Saccharomyces* yeast cells, and in particular strains of *Saccharomyces*, are known in the art and are described in, for example, Ausubel, F. M. et al. (1997), Current Protocols in Molecular Biology, Volume 2, pages 13.7.1 to 13.7.7, published by John Wiley & Sons Inc.

In one embodiment, a recombinant derivative of *Saccharomyces cerevisiae* strain MBG5151 or MBG5248 has been prepared by genetically modifying the strain (or another derivative thereof) to express a heterologous enzyme, such as an alpha-amylase and/or glucoamylase described herein (or any enzyme described in WO2020/023411, the content of which is incorporated herein by reference).

In one embodiment, is a method of producing a recombinant derivative of *Saccharomyces cerevisiae* strain MBG5151 (deposited under Accession No. NRRL Y-67971 at the Agricultural Research Service Patent Culture Collection (NRRL), Northern Regional Research Center, 1815 University Street, Peoria, IL, USA) comprising:

(a) transforming *Saccharomyces cerevisiae* strain MBG5151 (or a derivative of *Saccharomyces cerevisiae* strain MBG5151) with one or more expression vectors encoding a heterologous enzymes, such as a glucoamylase and/or an alpha-amylase; and (b) isolating the transformed strain.

In one embodiment, a derivative of *Saccharomyces cerevisiae* strain MBG5151 may be prepared by:

(a) culturing a first yeast strain with a second yeast strain, wherein the second yeast strain is *Saccharomyces cerevisiae* strain MBG5151 (or a derivative of *Saccharomyces cerevisiae* strain MBG5151), under conditions which permit combining of DNA between the first yeast strain and the second yeast strain; and (b) isolating hybrid strains; and (c) optionally repeating steps (a) and (b) using a hybrid strain isolated in step (b) as the first yeast strain and/or the derivative of *Saccharomyces cerevisiae* strain MBG5151.

In one embodiment, is a method of producing a recombinant derivative of *Saccharomyces cerevisiae* strain MBG5248 (deposited under Accession No. NRRL Y-68015 at the Agricultural Research Service Patent Culture Collection (NRRL), Northern Regional Research Center, 1815 University Street, Peoria, IL, USA) comprising:

(a) transforming *Saccharomyces cerevisiae* strain MBG5248 (or a derivative of *Saccharomyces cerevisiae* strain MBG5248) with one or more expression vectors encoding a heterologous enzymes, such as a glucoamylase and/or an alpha-amylase; and (b) isolating the transformed strain.

In one embodiment, a derivative of *Saccharomyces cerevisiae* strain MBG5248 may be prepared by:

(a) culturing a first yeast strain with a second yeast strain, wherein the second yeast strain is *Saccharomyces cerevisiae* strain MBG5248 (or a derivative of *Saccharomyces cerevisiae* strain MBG5248), under conditions which permit combining of DNA between the first yeast strain and the second yeast strain; and (b) isolating hybrid strains; and (c) optionally repeating steps (a) and (b) using a hybrid strain isolated in step (b) as the first yeast strain and/or the derivative of *Saccharomyces cerevisiae* strain MBG5248.

In some embodiments, the derivative of *Saccharomyces cerevisiae* strain MBG5151 or MBG5248 expresses a glucoamylase and/or an alpha-amylase. The derivatives expressing glucoamylase and/or alpha-amylase have been generated in order to improve ethanol yield and to improve process economy by cutting enzyme costs since part or all of the necessary enzymes needed to hydrolyse starch will be produced by the yeast organism.

Compositions

This aspect relates to a formulated *Saccharomyces* yeast composition comprising a yeast strain described herein and a naturally occurring and/or a nonenaturally occurring component.

In one embodiment, is a composition comprising *Saccharomyces cerevisiae* strain MBG5151 (or a derivative of *Saccharomyces cerevisiae* strain MBG5151) or *Saccharomyces cerevisiae* strain MBG5248 (or a derivative of *Saccharomyces cerevisiae* strain MBG5248). The composition may be, for example, cream yeast, compressed yeast, wet yeast, dry yeast, semi-dried yeast, crumble yeast, stabilized liquid yeast or frozen yeast. Methods for preparing such yeast compositions are known in the art.

In one embodiment, the *Saccharomyces cerevisiae* yeast strain is dry yeast, such as active dry yeast or instant yeast. In one embodiment, the *Saccharomyces cerevisiae* yeast strain is crumbled yeast. In one embodiment, the *Saccharomyces cerevisiae* yeast strain is compressed yeast. In one embodiment, the *Saccharomyces cerevisiae* yeast strain is a cream yeast.

In one embodiment, is a composition comprising a *Saccharomyces* yeast described herein, in particular *Saccharomyces cerevisiae* strain MBG5151 or MBG5248, and one or more of the component selected from the group consisting of: surfactants, emulsifiers, gums, swelling agent, and antioxidants and other processing aids.

Surfactant

The compositions described herein may comprise a *Saccharomyces* yeast described herein, in particular *Saccharomyces cerevisiae* strain MBG5151 or MBG5248, and any suitable surfactants. In one embodiment, the surfactant(s) is/are an anionic surfactant, cationic surfactant, and/or nonionic surfactant.

Emulsifier

The compositions described herein may comprise a *Saccharomyces* yeast described herein, in particular *Saccharomyces cerevisiae* strain MBG5151 or MBG5248, and any suitable emulsifier. In one embodiment, the emulsifier is a fatty-acid ester of sorbitan. In one embodiment, the emulsifier is selected from the group of sorbitan monostearate (SMS), citric acid esters of monodiglycerides, polyglycerolester, fatty acid esters of propylene glycol.

In one embodiment, the composition comprises a *Saccharomyces* yeast described herein, in particular *Saccharomyces cerevisiae* strain MBG5151 or MBG5248, and Olindronal SMS, Olindronal SK, or Olindronal SPL including composition concerned in European Patent No. 1,724,336 (hereby incorporated by reference). These products are commercially available from Bussetti, Austria, for active dry yeast.

Gum

The compositions described herein may comprise a *Saccharomyces* yeast described herein, in particular *Saccharomyces cerevisiae* strain MBG5151 or MBG5248, and any suitable gum. In one embodiment, the gum is selected from the group of carob, guar, tragacanth, arabic, xanthan and acacia gum, in particular for cream, compressed and dry yeast.

Swelling Agents

The compositions described herein may comprise a *Saccharomyces* yeast described herein, in particular *Saccharomyces cerevisiae* strain MBG5151 or MBG5248, and any suitable swelling agent. In one embodiment, the swelling agent is methyl cellulose or carboxymethyl cellulose.

Antioxidant

The compositions described herein may comprise a *Saccharomyces* yeast described herein, in particular *Saccharomyces cerevisiae* strain MBG5151 or MBG5248, and any suitable anti-oxidant. In one embodiment, the antioxidant is butylated hydroxyanisol (BHA) and/or butylated hydroxytoluene (BHT), or ascorbic acid (vitamin C), particular for active dry yeast.

Methods using a Cellulosic-Containing Material

In some embodiments, the methods described herein produce a fermentation product from a cellulosic-containing material. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic-containing material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one embodiment, the cellulosic-containing material is any biomass material. In another embodiment, the cellulosic-containing material is lignocellulose, which comprises cellulose, hemicelluloses, and lignin.

In one embodiment, the cellulosic-containing material is agricultural residue, herbaceous material (including energy crops), municipal solid waste, pulp and paper mill residue, waste paper, or wood (including forestry residue).

In another embodiment, the cellulosic-containing material is arundo, bagasse, bamboo, corn cob, corn fiber, corn stover, miscanthus, rice straw, switchgrass, or wheat straw.

In another embodiment, the cellulosic-containing material is aspen, eucalyptus, fir, pine, poplar, spruce, or willow.

In another embodiment, the cellulosic-containing material is algal cellulose, bacterial cellulose, cotton linter, filter paper, microcrystalline cellulose (e.g., AVICEL®), or phosphoric-acid treated cellulose.

In another embodiment, the cellulosic-containing material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic-containing material may be used as is or may be subjected to pretreatment, using conventional methods known in the art, as described herein. In a preferred embodiment, the cellulosic-containing material is pretreated.

The methods of using cellulosic-containing material can be accomplished using methods conventional in the art. Moreover, the methods of can be implemented using any conventional biomass processing apparatus configured to carry out the processes.

Cellulosic Pretreatment

In one embodiment, the cellulosic-containing material is pretreated before saccharification.

In practicing the processes described herein, any pretreatment process known in the art can be used to disrupt plant cell wall components of the cellulosic-containing material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: $10^{-18}$; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

In one embodiment, the cellulosic-containing material is pretreated before saccharification (i.e., hydrolysis) and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

In one embodiment, the cellulosic-containing material is pretreated with steam. In steam pretreatment, the cellulosic-containing material is heated to disrupt the plant cell wall components, including lignin, hemicellulose, and cellulose to make the cellulose and other fractions, e.g., hemicellulose, accessible to enzymes. The cellulosic-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

In one embodiment, the cellulosic-containing material is subjected to a chemical pretreatment. The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, *Bioresource Technology* 855: 1-33; Schell et al., 2004, *Bioresource Technology* 91: 179-188; Lee et al., 1999, *Adv. Biochem. Eng. Biotechnol.* 65: 93-115). In a specific embodiment the dilute acid pretreatment of cellulosic-containing material is carried out using 4% w/w sulfuric acid at 180° C. for 5 minutes.

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment. Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO2006/110891, WO2006/110899, WO2006/110900, and WO2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO2006/032282).

Ammonia fiber expansion (AFEX) involves treating the cellulosic-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and US2002/0164730.

In one embodiment, the chemical pretreatment is carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one embodiment, the acid concentration is in the range from preferably 0.01 to 10 wt. % acid, e.g., 0.05 to 5 wt. % acid or 0.1 to 2 wt. % acid. The acid is contacted with the cellulosic-containing material and held at a temperature in the range of preferably 140-200° C., e.g., 165-190° C., for periods ranging from 1 to 60 minutes.

In another embodiment, pretreatment takes place in an aqueous slurry. In preferred embodiments, the cellulosic-containing material is present during pretreatment in amounts preferably between $10^{-80}$ wt. %, e.g., 20-70 wt. % or 30-60 wt. %, such as around 40 wt. %. The pretreated cellulosic-containing material can be unwashed or washed using any method known in the art, e.g., washed with water.

In one embodiment, the cellulosic-containing material is subjected to mechanical or physical pretreatment. The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one embodiment, high pressure means pressure in the range of preferably about 100 to about 400 psi, e.g., about 150 to about 250 psi. In another embodiment, high temperature means temperature in the range of about 100 to about 300° C., e.g., about 140 to about 200° C. In a preferred embodiment, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in one embodiment, the cellulosic-containing material is subjected to physical (mechanical) or chemical pretreatment, or any combination thereof, to promote the separation and/or release of cellulose, hemicellulose, and/or lignin.

In one embodiment, the cellulosic-containing material is subjected to a biological pretreatment. The term "biological pretreatment" refers to any biological pretreatment that promotes the separation and/or release of cellulose, hemicellulose, and/or lignin from the cellulosic-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, DC, 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, DC, chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification and Fermentation of Cellulosic-Containing Material

Saccharification (i.e., hydrolysis) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF).

SHF uses separate process steps to first enzymatically hydrolyze the cellulosic-containing material to fermentable sugars, e.g., glucose, cellobiose, and pentose monomers, and then ferment the fermentable sugars to ethanol. In SSF, the enzymatic hydrolysis of the cellulosic-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, DC, 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation organismcan tolerate. It is understood herein that any method known in the art comprising pretreatment, enzymatic hydrolysis (saccharification), fermentation, or a combination thereof, can be used in the practicing the processes described herein.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

In the saccharification step (i.e., hydrolysis step), the cellulosic and/or starch-containing material, e.g., pretreated, is hydrolyzed to break down cellulose, hemicellulose, and/or starch to fermentable sugars, such as glucose, cellobiose, xylose, xylulose, arabinose, mannose, galactose, and/or soluble oligosaccharides. The hydrolysis is performed enzymatically e.g., by a cellulolytic enzyme composition. The enzymes of the compositions can be added simultaneously or sequentially.

Enzymatic hydrolysis may be carried out in a suitable aqueous environment under conditions that can be readily determined by one skilled in the art. In one embodiment, hydrolysis is performed under conditions suitable for the activity of the enzymes(s), i.e., optimal for the enzyme(s). The hydrolysis can be carried out as a fed batch or continuous process where the cellulosic and/or starch-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

Saccharification in may be carried out using a cellulolytic enzyme composition. Such enzyme compositions are described below in the "Cellulolytic Enzyme Composition'-section below. The cellulolytic enzyme compositions can comprise any protein useful in degrading the cellulosic-containing material. In one embodiment, the cellulolytic enzyme composition comprises or further comprises one or more (e.g., several) proteins selected from the group consisting of a cellulase, an AA9 (GH61) polypeptide, a hemicellulase, an esterase, an expansin, a ligninolytic enzyme, an oxidoreductase, a pectinase, a protease, and a swollenin.

In another embodiment, the cellulase is preferably one or more (e.g., several) enzymes selected from the group consisting of an endoglucanase, a cellobiohydrolase, and a beta-glucosidase.

In another embodiment, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another embodiment, the oxidoreductase is one or more (e.g., several) enzymes selected from the group consisting of a catalase, a laccase, and a peroxidase.

The enzymes or enzyme compositions used in a processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

In one embodiment, an effective amount of cellulolytic or hemicellulolytic enzyme composition to the cellulosic-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic-containing material.

In one embodiment, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another embodiment, an effective amount of such a compound is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc. under conditions as described in WO2012/021401, and the soluble contents thereof. A liquor for cellulolytic enhancement of an AA9 polypeptide (GH61 polypeptide) can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one embodiment, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In the fermentation step, sugars, released from the cellulosic-containing material, e.g., as a result of the pretreatment and enzymatic hydrolysis steps, are fermented to ethanol, by a fermenting organism, such as yeast described herein. Hydrolysis (saccharification) and fermentation can be separate or simultaneous.

Any suitable hydrolyzed cellulosic-containing material can be used in the fermentation step in practicing the processes described herein. Such feedstocks include, but are not limited to carbohydrates (e.g., lignocellulose, xylans, cellulose, starch, etc.). The material is generally selected based on economics, i.e., costs per equivalent sugar potential, and recalcitrance to enzymatic conversion.

Production of ethanol by a fermenting organism using cellulosic-containing material results from the metabolism of sugars (monosaccharides). The sugar composition of the hydrolyzed cellulosic-containing material and the ability of the fermenting organism to utilize the different sugars has a direct impact in process yields.

Compositions of the fermentation media and fermentation conditions depend on the fermenting organism and can easily be determined by one skilled in the art. Typically, the fermentation takes place under conditions known to be suitable for generating the fermentation product. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the fermenting organism as an electron and hydrogen acceptor in order to generate NAD+.

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

A fermentation stimulator can be used in a process described herein to further improve the fermentation, and in particular, the performance of the fermenting organism, such as, rate enhancement and product yield (e.g., ethanol yield). A "fermentation stimulator" refers to stimulators for growth of the fermenting organisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Cellulolytic Enzymes and Compositions

A cellulolytic enzyme or cellulolytic enzyme composition may be present and/or added during saccharification. A cellulolytic enzyme composition is an enzyme preparation containing one or more (e.g., several) enzymes that hydrolyze cellulosic-containing material. Such enzymes include endoglucanase, cellobiohydrolase, beta-glucosidase, and/or combinations thereof.

In some embodiments, the fermenting organism comprises one or more (e.g., several) heterologous polynucleotides encoding enzymes that hydrolyze cellulosic-containing material (e.g., an endoglucanase, cellobiohydrolase, beta-glucosidase or combinations thereof). Any enzyme described or referenced herein that hydrolyzes cellulosic-containing material is contemplated for expression in the fermenting organism.

The cellulolytic enzyme may be any cellulolytic enzyme that is suitable for the expression in the fermenting organism and/or the methods described herein (e.g., an endoglucanase, cellobiohydrolase, beta-glucosidase), such as a naturally occurring cellulolytic enzyme or a variant thereof that retains cellulolytic enzyme activity.

In some embodiments, the fermenting organism comprising a heterologous polynucleotide encoding a cellulolytic enzyme has an increased level of cellulolytic enzyme activity (e.g., increased endoglucanase, cellobiohydrolase, and/or beta-glucosidase) compared to the fermenting organisms without the heterologous polynucleotide encoding the cellulolytic enzyme, when cultivated under the same conditions. In some embodiments, the fermenting organism has an increased level of cellulolytic enzyme activity of at least 5%, e.g., at least 10%, at least 15%, at least 20%, at least 25%, at least 50%, at least 100%, at least 150%, at least 200%, at least 300%, or at 500% compared to the fermenting organism without the heterologous polynucleotide encoding the cellulolytic enzyme, when cultivated under the same conditions.

Exemplary cellulolytic enzymes that can be used with the fermenting organisms and/or the methods described herein include bacterial, yeast, or filamentous fungal cellulolytic enzymes, e.g., obtained from any of the microorganisms described or referenced herein, as described supra under the sections related to proteases.

The cellulolytic enzyme may be of any origin. In one embodiment, the cellulolytic enzyme is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*. In a preferred embodiment the cellulolytic enzyme is derived from a strain of *Trichoderma reesei*.

The cellulolytic enzyme composition may further comprise one or more of the following polypeptides, such as enzymes: AA9 polypeptide (GH61 polypeptide) having cellulolytic enhancing activity, beta-glucosidase, xylanase, beta-xylosidase, CBH I, CBH II, or a mixture of two, three, four, five or six thereof.

The further polypeptide(s) (e.g., AA9 polypeptide) and/or enzyme(s) (e.g., beta-glucosidase, xylanase, beta-xylosidase, CBH I and/or CBH II may be foreign to the cellulolytic enzyme composition producing organism (e.g., *Trichoderma reesei*).

In one embodiment, the cellulolytic enzyme composition comprises an AA9 polypeptide having cellulolytic enhancing activity and a beta-glucosidase.

In another embodiment the cellulolytic enzyme composition comprises an AA9 polypeptide having cellulolytic enhancing activity, a beta-glucosidase, and a CBH I.

In another embodiment the cellulolytic enzyme composition comprises an AA9 polypeptide having cellulolytic enhancing activity, a beta-glucosidase, a CBH I and a CBH II. Other enzymes, such as endoglucanases, may also be comprised in the cellulolytic enzyme composition.

As mentioned above the cellulolytic enzyme composition may comprise a number of difference polypeptides, including enzymes.

In one embodiment, the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO2005/074656), and *Aspergillus oryzae* beta-glucosidase fusion protein (e.g., one disclosed in WO2008/057637, in particular shown as SEQ ID NOs: 59 and 60).

In another embodiment the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO2005/074656), and *Aspergillus fumigatus* beta-glucosidase (e.g., SEQ ID NO: 2 of WO2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, and *Aspergillus fumigatus* beta-glucosidase (e.g., SEQ ID NO: 2 of WO2005/047499).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, and *Aspergillus fumigatus* beta-glucosidase (e.g., SEQ ID NO: 2 of WO2005/047499) or a variant disclosed in WO2012/044915 (hereby incorporated by reference), in particular one comprising one or more such as all of the following substitutions: F100D, S283G, N456E, F512Y.

In one embodiment, the cellulolytic enzyme composition is a *Trichoderma reesei* cellulolytic composition, further comprising an AA9 (GH61A) polypeptide having cellulolytic enhancing activity, in particular the one derived from a strain of *Penicillium emersonii* (e.g., SEQ ID NO: 2 in WO2011/041397), *Aspergillus fumigatus* beta-glucosidase (e.g., SEQ ID NO: 2 in WO2005/047499) variant with one or more, in particular all of the following substitutions: F100D, S283G, N456E, F512Y and disclosed in WO2012/044915; *Aspergillus fumigatus* Cel7A CBH1, e.g., the one disclosed as SEQ ID NO: 6 in WO2011/057140 and *Aspergillus fumigatus* CBH II, e.g., the one disclosed as SEQ ID NO: 18 in WO2011/057140.

In a preferred embodiment the cellulolytic enzyme composition is a *Trichoderma reesei*, cellulolytic enzyme composition, further comprising a hemicellulase or hemicellulolytic enzyme composition, such as an *Aspergillus fumigatus* xylanase and *Aspergillus fumigatus* beta-xylosidase.

In one embodiment, the cellulolytic enzyme composition also comprises a xylanase (e.g., derived from a strain of the genus *Aspergillus*, in particular *Aspergillus aculeatus* or *Aspergillus fumigatus*; or a strain of the genus *Talaromyces*, in particular *Talaromyces leycettanus*) and/or a beta-xylosidase (e.g., derived from *Aspergillus*, in particular *Aspergillus fumigatus*, or a strain of *Talaromyces*, in particular *Talaromyces emersonii*).

In one embodiment, the cellulolytic enzyme composition is a *Trichoderma reesei* cellulolytic enzyme composition, further comprising *Thermoascus aurantiacus* AA9 (GH61A) polypeptide having cellulolytic enhancing activity (e.g., WO2005/074656), *Aspergillus oryzae* beta-glucosidase fusion protein (e.g., one disclosed in WO2008/057637, in particular as SEQ ID NOs: 59 and 60), and *Aspergillus aculeatus* xylanase (e.g., Xyl II in WO94/21785).

In another embodiment the cellulolytic enzyme composition comprises a *Trichoderma reesei* cellulolytic preparation, further comprising *Thermoascus aurantiacus* GH61A polypeptide having cellulolytic enhancing activity (e.g., SEQ ID NO: 2 in WO2005/074656), *Aspergillus fumigatus* beta-glucosidase (e.g., SEQ ID NO: 2 of WO2005/047499) and *Aspergillus aculeatus* xylanase (Xyl II disclosed in WO94/21785).

In another embodiment the cellulolytic enzyme composition comprises a *Trichoderma reesei* cellulolytic enzyme composition, further comprising *Thermoascus aurantiacus* AA9 (GH61A) polypeptide having cellulolytic enhancing activity (e.g., SEQ ID NO: 2 in WO2005/074656), *Aspergillus fumigatus* beta-glucosidase (e.g., SEQ ID NO: 2 of WO2005/047499) and *Aspergillus aculeatus* xylanase (e.g., Xyl II disclosed in WO94/21785).

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499) and *Aspergillus fumigatus* xylanase (e.g., Xyl III in WO2006/078256).

In another embodiment the cellulolytic enzyme composition comprises a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499), *Aspergillus fumigatus* xylanase (e.g., Xyl III in WO2006/078256), and CBH I from *Aspergillus fumigatus*, in particular Cel7A CBH1 disclosed as SEQ ID NO: 2 in WO2011/057140.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499), *Aspergillus fumigatus* xylanase (e.g., Xyl III in WO2006/078256), CBH I from *Aspergillus fumigatus*, in particular Cel7A CBH1 disclosed as SEQ ID NO: 2 in WO2011/057140, and CBH II derived from *Aspergillus fumigatus* in particular the one disclosed as SEQ ID NO: 4 in WO2013/028928.

In another embodiment the cellulolytic enzyme composition is a *Trichoderma reesei* cellulolytic enzyme composition, further comprising *Penicillium emersonii* AA9 (GH61A) polypeptide having cellulolytic enhancing activity, in particular the one disclosed in WO2011/041397, *Aspergillus fumigatus* beta-glucosidase (e.g., SEQ ID NO: 2 of WO2005/047499) or variant thereof with one or more, in particular all, of the following substitutions: F100D, S283G, N456E, F512Y; *Aspergillus fumigatus* xylanase (e.g., Xyl III in WO2006/078256), CBH I from *Aspergillus fumigatus*, in particular Cel7A CBH I disclosed as SEQ ID NO: 2 in WO2011/057140, and CBH II derived from *Aspergillus fumigatus*, in particular the one disclosed in WO2013/028928.

In another embodiment the cellulolytic enzyme composition is a *Trichoderma reesei* cellulolytic enzyme composition comprising the CBH I (GENSEQP Accession No. AZY49536 (WO2012/103293); a CBH II (GENSEQP Accession No. AZY49446 (WO2012/103288); a beta-glucosidase variant (GENSEQP Accession No. AZU67153 (WO2012/44915)), in particular with one or more, in particular all, of the following substitutions: F100D, S283G, N456E, F512Y; and AA9 (GH61 polypeptide) (GENSEQP Accession No. BAL61510 (WO2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288); a GH10 xylanase (GENSEQP Accession No. BAK46118 (WO2013/019827)); and a beta-xylosidase (GENSEQP Accession No. AZI04896 (WO2011/057140)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)); and an AA9 (GH61 polypeptide; GENSEQP Accession No. BAL61510 (WO2013/028912)).

In another embodiment the cellulolytic enzyme composition is a *Trichoderma reesei* cellulolytic enzyme composition comprising a CBH I (GENSEQP Accession No. AZY49536 (WO2012/103293)); a CBH II (GENSEQP Accession No. AZY49446 (WO2012/103288)), an AA9 (GH61 polypeptide; GENSEQP Accession No. BAL61510 (WO2013/028912)), and a catalase (GENSEQP Accession No. BAC11005 (WO2012/130120)).

In one embodiment, the cellulolytic enzyme composition is a *Trichoderma reesei* cellulolytic enzyme composition comprising a CBH I (GENSEQP Accession No. AZY49446 (WO2012/103288); a CBH II (GENSEQP Accession No. AZY49446 (WO2012/103288)), a beta-glucosidase variant (GENSEQP Accession No. AZU67153 (WO2012/44915)), with one or more, in particular all, of the following substitutions: F100D, S283G, N456E, F512Y; an AA9 (GH61 polypeptide; GENSEQP Accession No. BAL61510 (WO2013/028912)), a GH10 xylanase (GENSEQP Accession No. BAK46118 (WO2013/019827)), and a beta-xylosidase (GENSEQP Accession No. AZI04896 (WO2011/057140)).

In one embodiment, the cellulolytic composition is a *Trichoderma reesei* cellulolytic enzyme preparation comprising an EG I (Swissprot Accession No. P07981), EG II (EMBL Accession No. M19373), CBH I (supra); CBH II (supra); beta-glucosidase variant (supra) with the following substitutions: F100D, S283G, N456E, F512Y; an AA9 (GH61 polypeptide; supra), GH10 xylanase (supra); and beta-xylosidase (supra).

All cellulolytic enzyme compositions disclosed in WO2013/028928 are also contemplated and hereby incorporated by reference.

The cellulolytic enzyme composition comprises or may further comprise one or more (several) proteins selected from the group consisting of a cellulase, a AA9 (i.e., GH61) polypeptide having cellulolytic enhancing activity, a hemicellulase, an expansin, an esterase, a laccase, a ligninolytic enzyme, a pectinase, a peroxidase, a protease, and a swollenin.

In one embodiment, the cellulolytic enzyme composition is a commercial cellulolytic enzyme composition. Examples of commercial cellulolytic enzyme compositions suitable for use in a process of the invention include: CELLIC® CTec (Novozymes A/S), CELLIC® CTec2 (Novozymes A/S), CELLIC® CTec3 (Novozymes A/S), CELLUCLAST™ (Novozymes A/S), SPEZYME™ CP (Genencor Int.), ACCELLERASE™ 1000, ACCELLERASE 1500, ACCELLERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme composition may be added in an amount effective from about 0.001 to about 5.0 wt. % of solids, e.g., about 0.025 to about 4.0 wt. % of solids or about 0.005 to about 2.0 wt. % of solids.

Additional enzymes, and compositions thereof can be found in WO2011/153516 and WO2016/045569 (the contents of which are incorporated herein).

Additional polynucleotides encoding suitable cellulolytic enzymes may be obtained from microorganisms of any genus, including those readily available within the UniProtKB database (www.uniprot.org).

The cellulolytic enzyme coding sequences can also be used to design nucleic acid probes to identify and clone DNA encoding cellulolytic enzymes from strains of different genera or species are known in the art.

The polynucleotides encoding cellulolytic enzymes may also be identified and obtained from other sources including microorganisms isolated from nature (e.g., soil, composts, water, etc.) or DNA samples obtained directly from natural materials (e.g., soil, composts, water, etc.) are known in the art.

Techniques used to isolate or clone polynucleotides encoding cellulolytic enzymes are known in the art.

In one embodiment, the cellulolytic enzyme has a mature polypeptide sequence of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any cellulolytic enzyme described or referenced herein (e.g., any endoglucanase, cellobiohydrolase, or beta-glucosidase). In one embodiment, the cellulolytic enzyme ha a mature polypeptide sequence that differs by no more than ten amino acids, e.g., by no more than five amino acids, by no more than four amino acids, by no more than three amino acids, by no more than two amino acids, or by one amino acid from any cellulolytic enzyme described or referenced herein. In one embodiment, the cellulolytic enzyme has a mature polypeptide sequence that comprises or consists of the amino acid sequence of any cellulolytic enzyme described or referenced herein, allelic variant, or a fragment thereof having cellulolytic enzyme activity. In one embodiment, the cellulolytic enzyme has an amino acid substitution, deletion, and/or insertion of one or more (e.g., two, several) amino acids. In some embodiments, the total number of amino acid substitutions, deletions and/or insertions is not more than 10, e.g., not more than 9, 8, 7, 6, 5, 4, 3, 2, or 1.

In some embodiments, the cellulolytic enzyme has at least 20%, e.g., at least 40%, at least 50%, at least 60%, at least 70%, at least 80%, at least 90%, at least 95%, at least 96%, at least 97%, at least 98%, at least 99%, or 100% of the cellulolytic enzyme activity of any cellulolytic enzyme described or referenced herein (e.g., any endoglucanase, cellobiohydrolase, or beta-glucosidase) under the same conditions.

In one embodiment, the cellulolytic enzyme coding sequence hybridizes under at least low stringency conditions, e.g., medium stringency conditions, medium-high stringency conditions, high stringency conditions, or very high stringency conditions with the full-length complementary strand of the coding sequence from any cellulolytic enzyme described or referenced herein (e.g., any endoglucanase, cellobiohydrolase, or beta-glucosidase). In one embodiment, the cellulolytic enzyme coding sequence has at least 65%, e.g., at least 70%, at least 75%, at least 80%, at least 85%, at least 85%, at least 90%, at least 91%, at least 92%, at least 93%, at least 94%, at least 95%, at least 96%, at least 97%, at least 98%, at least 99%, or 100% sequence identity with the coding sequence from any cellulolytic enzyme described or referenced herein.

In one embodiment, the polynucleotide encoding the cellulolytic enzyme comprises the coding sequence of any cellulolytic enzyme described or referenced herein (e.g., any endoglucanase, cellobiohydrolase, or beta-glucosidase). In one embodiment, the polynucleotide encoding the cellulolytic enzyme comprises a subsequence of the coding sequence from any cellulolytic enzyme described or referenced herein, wherein the subsequence encodes a polypeptide having cellulolytic enzyme activity. In one embodiment, the number of nucleotides residues in the subsequence is at least 75%, e.g., at least 80%, 85%, 90%, or 95% of the number of the referenced coding sequence.

The cellulolytic enzyme can also include fused polypeptides or cleavable fusion polypeptides.

Methods using a Starch-Containing Material

In some embodiments, the methods described herein produce a fermentation product from a starch-containing material. Starch-containing material is well-known in the art, containing two types of homopolysaccharides (amylose and amylopectin) and is linked by alpha-(1-4)-D-glycosidic bonds. Any suitable starch-containing starting material may be used. The starting material is generally selected based on the desired fermentation product, such as ethanol. Examples of starch-containing starting materials include cereal, tubers or grains. Specifically, the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In one embodiment, the starch-containing starting material is corn. In one embodiment, the starch-containing starting material is wheat. In one embodiment, the starch-containing starting material is barley. In one embodiment, the starch-containing starting material is rye. In one embodiment, the starch-containing starting material is milo. In one embodiment, the starch-containing starting material is sago. In one embodiment, the starch-containing starting material is cassava. In one embodiment, the starch-containing starting material is tapioca. In one embodiment, the starch-containing starting material is sorghum. In one embodiment, the starch-containing starting material is rice. In one embodiment, the starch-containing starting material is peas. In one embodiment, the starch-containing starting material is beans. In one embodiment, the starch-containing starting material is sweet potatoes. In one embodiment, the starch-containing starting material is oats.

The methods using a starch-containing material may include a conventional process (e.g., including a liquefaction step described in more detail below) or a raw starch hydrolysis process. In some embodiments using a starch-containing material, saccharification of the starch-containing material is at a temperature above the initial gelatinization temperature. In some embodiments using a starch-containing material, saccharification of the starch-containing material is at a temperature below the initial gelatinization temperature.

Liquefaction

In embodiments using a starch-containing material, the methods may further comprise a liquefaction step carried out by subjecting the starch-containing material at a temperature above the initial gelatinization temperature to an alpha-amylase and optionally a protease and/or a glucoamylase. Other enzymes such as a pullulanase and phytase may also be present and/or added in liquefaction. In some embodiments, the liquefaction step is carried out prior to steps a) and b) of the described methods.

Liquefaction step may be carried out for 0.5-5 hours, such as 1-3 hours, such as typically about 2 hours.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. The initial gelatinization temperature of a given starch-containing material may be determined as the temperature at which birefringence is lost in 5% of the starch granules using the method described by Gorinstein and Lii, 1992, *Starch/Starke* 44(12): 461-466.

Liquefaction is typically carried out at a temperature in the range from 70-100° C. In one embodiment, the temperature in liquefaction is between 75-95° C., such as between 75-90° C., between 80-90° C., or between 82-88° C., such as about 85° C.

A jet-cooking step may be carried out prior to liquefaction in step, for example, at a temperature between 110-145° C., 120-140° C., 125-135° C., or about 130° C. for about 1-15 minutes, for about 3-10 minutes, or about 5 minutes.

The pH during liquefaction may be between 4 and 7, such as pH 4.5-6.5, pH 5.0-6.5, pH 5.0-6.0, pH 5.2-6.2, or about 5.2, about 5.4, about 5.6, or about 5.8.

In one embodiment, the process further comprises, prior to liquefaction, the steps of:

i) reducing the particle size of the starch-containing material, preferably by dry milling;
ii) forming a slurry comprising the starch-containing material and water.

The starch-containing starting material, such as whole grains, may be reduced in particle size, e.g., by milling, in order to open up the structure, to increase surface area, and allowing for further processing. Generally, there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. In one embodiment, the starch-containing material is subjected to dry milling. In one embodiment, the particle size is reduced to between 0.05 to 3.0 mm, e.g., 0.1-0.5 mm, or so that at least 30%, at least 50%, at least 70%, or at least 90% of the starch-containing material fit through a sieve with a 0.05 to 3.0 mm screen, e.g., 0.1-0.5 mm screen. In another embodiment, at least 50%, e.g., at least 70%, at least 80%, or at least 90% of the starch-containing material fit through a sieve with #6 screen.

The aqueous slurry may contain from $10^{-55}$ w/w-% dry solids (DS), e.g., 25-45 w/w-% dry solids (DS), or 30-40 w/w-% dry solids (DS) of starch-containing material.

The alpha-amylase, optionally a protease, and optionally a glucoamylase may initially be added to the aqueous slurry to initiate liquefaction (thinning). In one embodiment, only a portion of the enzymes (e.g., about ⅓) is added to the aqueous slurry, while the rest of the enzymes (e.g., about ⅔) are added during liquefaction step.

Alpha-amylases and glucoamylases used in liquefaction can be found in the art, e.g., WO2020/023411 (the content of which is incorporated herein by reference). Likewise, examples of suitable proteases used in liquefaction can be found in the art, e.g. WO2018/222990 (the content of which is incorporated herein by reference).

Saccharification and Fermentation of Starch-Containing Material

In embodiments using a starch-containing material, a glucoamylase may be present and/or added in saccharification step a) and/or fermentation step b) or simultaneous saccharification and fermentation (SSF). The glucoamylase of the saccharification step a) and/or fermentation step b) or simultaneous saccharification and fermentation (SSF) is typically different from the glucoamylase optionally added to any liquefaction step described supra. In one embodiment, the glucoamylase is present and/or added together with a fungal alpha-amylase. Suitable glucoamylases used in saccharification or SSF can be found in the art, e.g., WO2020/023411 (the content of which is incorporated herein by reference).

When doing sequential saccharification and fermentation, saccharification step a) may be carried out under conditions well-known in the art. For instance, saccharification step a) may last up to from about 24 to about 72 hours. In one embodiment, pre-saccharification is done. Pre-saccharification is typically done for 40-90 minutes at a temperature between 30-65° C., typically about 60° C. Pre-saccharification is, in one embodiment, followed by saccharification during fermentation in simultaneous saccharification and fermentation (SSF). Saccharification is typically carried out at temperatures from 20-75° C., preferably from 40-70° C., typically about 60° C., and typically at a pH between 4 and 5, such as about pH 4.5.

Fermentation is carried out in a fermentation medium, as known in the art and, e.g., as described herein. The fermentation medium includes the fermentation substrate, that is, the carbohydrate source that is metabolized by the fermenting organism. With the processes described herein, the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Generally, fermenting organisms such as yeast, including *Saccharomyces cerevisiae* yeast, require an adequate source of nitrogen for propagation and fermentation. Many sources of supplemental nitrogen, if necessary, can be used and such sources of nitrogen are well known in the art. The nitrogen source may be organic, such as urea, DDGs, wet cake or corn mash, or inorganic, such as ammonia or ammonium hydroxide. In one embodiment, the nitrogen source is urea.

Fermentation can be carried out under low nitrogen conditions, e.g., when using a protease-expressing yeast. In some embodiments, the fermentation step is conducted with less than 1000 ppm supplemental nitrogen (e.g., urea or ammonium hydroxide), such as less than 750 ppm, less than 500 ppm, less than 400 ppm, less than 300 ppm, less than 250 ppm, less than 200 ppm, less than 150 ppm, less than 100 ppm, less than 75 ppm, less than 50 ppm, less than 25 ppm, or less than 10 ppm, supplemental nitrogen. In some embodiments, the fermentation step is conducted with no supplemental nitrogen.

Simultaneous saccharification and fermentation ("SSF") is widely used in industrial scale fermentation product production processes, especially ethanol production processes. When doing SSF the saccharification step a) and the fermentation step b) are carried out simultaneously. There is no holding stage for the saccharification, meaning that a fermenting organism, such as yeast, and enzyme(s), may be added together. However, it is also contemplated to add the fermenting organism and enzyme(s) separately. SSF is typically carried out at a temperature from 25° C. to 40° C., such as from 28° C. to 35° C., such as from 30° C. to 34° C., or about 32° C. In one embodiment, fermentation is ongoing for 6 to 120 hours, in particular 24 to 96 hours. In one embodiment, the pH is between 4-5.

In one embodiment, a cellulolytic enzyme composition is present and/or added in saccharification, fermentation or simultaneous saccharification and fermentation (SSF). Examples of such cellulolytic enzyme compositions can be found in the "Cellulolytic Enzymes and Compositions" section. The cellulolytic enzyme composition may be present and/or added together with a glucoamylase, such as one disclosed in the "Glucoamylases" section.

Fermentation Products

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

In one embodiment, the fermentation product is an alcohol. The term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603. In one embodiment, the fermentation product is ethanol.

In another embodiment, the fermentation product is an alkane. The alkane may be an unbranched or a branched alkane. The alkane can be, but is not limited to, pentane, hexane, heptane, octane, nonane, decane, undecane, or dodecane.

In another embodiment, the fermentation product is a cycloalkane. The cycloalkane can be, but is not limited to, cyclopentane, cyclohexane, cycloheptane, or cyclooctane.

In another embodiment, the fermentation product is an alkene. The alkene may be an unbranched or a branched alkene. The alkene can be, but is not limited to, pentene, hexene, heptene, or octene.

In another embodiment, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another embodiment, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another embodiment, the fermentation product is isoprene.

In another embodiment, the fermentation product is a ketone. The term "ketone" encompasses a substance that contains one or more ketone moieties. The ketone can be, but is not limited to, acetone.

In another embodiment, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another embodiment, the fermentation product is polyketide.

Recovery

The fermentation product, e.g., ethanol, can optionally be recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

In some embodiments of the methods, the fermentation product after being recovered is substantially pure. With respect to the methods herein, "substantially pure" intends a recovered preparation that contains no more than 15% impurity, wherein impurity intends compounds other than the fermentation product (e.g., ethanol). In one variation, a substantially pure preparation is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of ethanol and contaminants, and sugar consumption can be performed using methods known in the art. For example, ethanol product, as well as other organic compounds, can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of ethanol in the fermentation broth can also be tested with the culture supernatant. Byproducts and residual sugar in the fermentation medium (e.g., glucose or xylose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

Deposit of Biological Material

The following biological material has been deposited under the terms of the Budapest Treaty with the Agricultural Research Service Patent Culture Collection (NRRL), Northern Regional Research Center, 1815 University Street, Peoria, IL, USA, and given the following accession number:

| Deposit | Accession Number | Date of Deposit |
|---|---|---|
| *Saccharomyces cerevisiae* strain MBG5151 | NRRL Y-67971 | Jul. 17, 2020 |
| *Saccharomyces cerevisiae* strain MBG5248 | NRRL Y-68015 | Mar. 5, 2021 |
| *Saccharomyces cerevisiae* strain CIBTS1260 | NRRL Y-50973 | Sep. 5, 2014 |

The strains were deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice.

The invention described and claimed herein is not to be limited in scope by the specific aspects or embodiments herein disclosed, since these aspects/embodiments are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. All references are specifically incorporated by reference for that which is described.

The following examples are offered to illustrate certain aspects/embodiments of the present invention, but not in any way intended to limit the scope of the invention as claimed.

EXAMPLES

Materials

Cellulolytic Enzyme Composition CA ("CA"): Cellulolytic enzyme preparation derived from *Trichoderma reesei* further comprising GH61A polypeptide having cellulolytic enhancing activity derived from a strain of *Penicillium emersonii* (SEQ ID NO: 2 in WO2011/041397), *Aspergillus fumigatus* beta-glucosidase (SEQ ID NO: 2 in WO2005/047499) variant F100D, S283G, N456E, F512Y) disclosed in WO2012/044915; *Aspergillus fumigatus* Cel7A CBH1 disclosed as SEQ ID NO: 6 in WO2011/057140 and *Aspergillus fumigatus* CBH II disclosed as SEQ ID NO: 18 in WO2011/057140. Further, Cellulolytic Enzyme Preparation CA further comprises 10% of a cellulolytic enzyme preparation from *Trichoderma reesei*, further comprising *Aspergillus fumigatus* xylanase (SEQ ID NO: 8 in WO2016/045569) and *Aspergillus fumigatus* beta-xylosidase (SEQ ID NO: 9 in WO2016/045569).

Cellulolytic Enzyme Composition CB ("CB"): *Trichoderma reesei* cellulolytic enzyme preparation comprising EG I of SEQ ID NO: 21 in WO2016/045569, EG II of SEQ ID NO: 22 in WO2016/045569, CBH I of SEQ ID NO: 14 in WO2016/045569; CBH II of SEQ ID NO: 15 of WO2016/045569; beta-glucosidase variant of SEQ ID NO: 5 of WO2016/045569 with the following substitutions: F100D, S283G, N456E, F512Y; the AA9 (GH61 polypeptide) of SEQ ID NO: 7 in WO2016/045569, GH10 xylanase of SEQ ID NO: 16 in WO2016/045569; and beta-xylosidase of SEQ ID NO: 17 in WO2016/045569.

BSGX001 is disclosed in U.S. Pat. No. 8,586,336-B2 (hereby incorporated by reference) and was constructed as follows: Host *Saccharomyces cerevisiae* strain BSPX042 (phenotype: ura3-251, overexpression of XKS1; overexpression of RPE1, RKI1, TAL1, and TKL1, which are genes in PPP; knockout of aldose reductase gene GRE3; and damage of electron transport respiratory chain by deleting gene COX4 after adaptive evolution), was transformed with vector pJFE3-RuXI inserted with xylose isomerase gene (SEQ ID NO: 1 in U.S. Pat. No. 8,586,336-B2 or SEQ ID NO: 20 herein) encoding the RuXI shown in SEQ ID NO: 2 in U.S. Pat. No. 8,586,336-B2.

MBG5147, MBG5148, MBG5149, MBG5150, MBG5151 were prepared from CIBTS1260 (See, WO2016/045569, the content of which is incorporated here by reference) in accordance with evolution and breeding procedures described in U.S. Pat. No. 8,257,959).

Example 1: Construction of the Strain CIBTS1000

A diploid *Saccharomyces cerevisiae* strain that is known to be an efficient ethanol producer from glucose was identified. *S. cerevisiae* strain CCTCC M94055 from the Chinese Center for Type Culture Collection (CCTCC) was used.

A xylose isomerase termed mgXI was cloned from a meta genomics project meaning that the donor organism is not known. The isolation and the characteristics of this xylose isomerase are described in CN patent application No. 102174549A or US patent Publication No. 2012/0225452.

A pentose transporter termed GXF was cloned from *Candida intermedia* using standard methods. This xylose transporter was described by D. Runquist et. al. (Runquist D, Fonseca C, Radstrom P, Spencer-Martins I, Hahn-Hagerdal B: "Expression of the Gxf1 transporter from *Candida intermedia* improves fermentation performance in recombinant xylose-utilizing *Saccharomyces cerevisiae*". Appl Microbiol Biotechnol 2009, 82:123-130).

A Zeocin resistance marker from *Streptoalloteichus hindustanus* for selection of Zeocin resistant *E. coli* or *S. cerevisiae* transformants. A double promoter was fused to the 5' end of the Zeocin gene consisting of an *S. cerevisiae* Translation Elongation Factor (TEF1) promoter and an *E. coli* EM7 promoter. The *S. cerevisiae* CYC1 terminator was added to the 3' end of the Zeocin gene. The entire Zeocin expression cassette was flanked by loxP sites to enable deletion of this expression cassette by Cre-lox recombination (B. Sauer: "*Functional expression of the Cre-Lox site specific recombination system in the yeast Saccharomyces cerevisiae*." Mol. Cell. Biol. 1987, 7: 2087-2096).

The xylose isomerase/pentose transporter expression plasmid was termed pYIE2-mgXI-GXF1-δ and is shown in FIG. 1.

The plasmid pYIE2-mgXI-GXF1-delta was first linierized by XhoI digestion and then transformed into the parental strain *Saccharomyces cerevisia* CCTCC M94055 following selection for zeocin resistant transformants. A strain termed CIBTS0912 was isolated having the plasmid integrated into a delta sequence. The zeocin resistance cassette located between the two loxP sites were then deleted by transient CRE recombinase expression resulting in the strain CIBTS0914.

Figure 2:
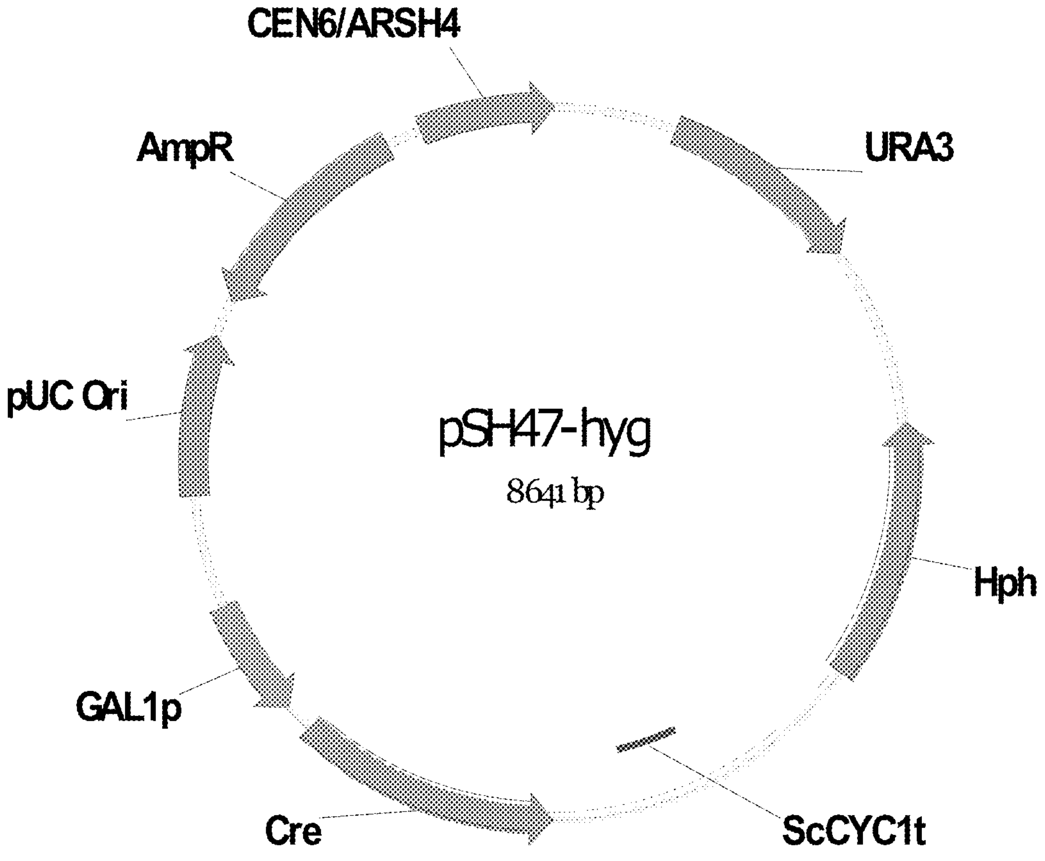
FIG. 2 shows a plasmid map of the plasmid used pSH47-hyg.

The transient CRE recombinase expression was achieved similar to the yeast standard method described by Prein et. al. (Prein B, Natter K, Kohlwein S D. "*A novel strategy for constructing N-terminal chromosomal fusions to green fluorescent protein in the yeast Saccharomyces cerevisiae*". FEBS Lett. 2000: 485, 29-34.) transforming with an unstable plasmid expressing the CRE recombinase followed by curing for that plasmid again. In this work the kanamycin gene of the yeast standard vector pSH47 was replaced with a hygromycin resistance marker so that rather than selecting for kanamycin resistance, selection for hygromycin was used. A plasmid map of the plasmid used pSH47-hyg is shown in FIG. 2. A table listing the genetic elements used is shown below in Table 1.

TABLE 1

| Gene/element name | Function | origin |
|---|---|---|
| Cre | Recombinase that catalyse recombination between lox sites | *Saccharomyces cerevisiae.* |
| GAL1p | Yeast promoter induced by galactose | *Saccharomyces cerevisiae.* |
| ScCYC1t | Yeast terminator | *Saccharomyces cerevisiae.* |
| hph | Hygromycin resistance gene. | *Streptomyces hygroscopicus.* |
| URA3 | Auxotrophic selection marker | *Saccharomyces cerevisiae.* |
| CEN6/ARSH4 | Replication origin | *Saccharomyces cerevisiae.* |
| pUC Ori | *E. coli* replication origin | *Escherichia coli* |
| AmpR | Ampicillin resistance gene | *Escherichia coli* |

The xylose isomerase gene was fused to the Triose Phosphate Isomerase (TPI) promoter from *Saccharomyces cerevisiae* and the TPI terminator using standard methods so that the expression of the xylose isomerase in *S. cerevisiae* was controlled by the TPI expression signals.

The GXF gene was fused to the TPI expression signals in the same way.

These two expression cassettes were inserted into an *Escherichia coli* cloning vector containing:

The *E. coli* colE1 origin of replication securing that the plasmid could be propagated in *E. coli.*

A delta (δ) sequence fragment from *Saccharomyces cerevisiae.*

The strain CIBTS0914 was transformed with XhoI digested pYIE2-mgXI-GXF1-δ again in order to increase the copy number of the two expression cassettes and a zeocin resistant strain, CIBTS0916 was selected.

In order to overexpress the genes of the pentose phosphate pathway, an expression plasmid harboring the selected pentose phosphate pathway genes was assembled. The genes selected for overexpression were:

1. Xylulo kinase (XKS1).
2. Trans-aldolase (TAL1).
3. Ribulose 5 phosphate epimerase (RPE1).
4. Trans-ketolase (TKL1).
5. Ribose 5 phosphate isomerase (RKI1)

In addition to these genes, the KanMX selection cassette surrounded by loxP sites was included as a part of the *E. coli—S. cerevisiae* shuttle vector pUG6 (Güldener U, Heck S, Fielder T, Beinhauer J, Hegemann J H. "*A new efficient gene disruption cassette for repeated use in budding yeast.*" NAR 1996, 24:2519-24).

Figure 3:
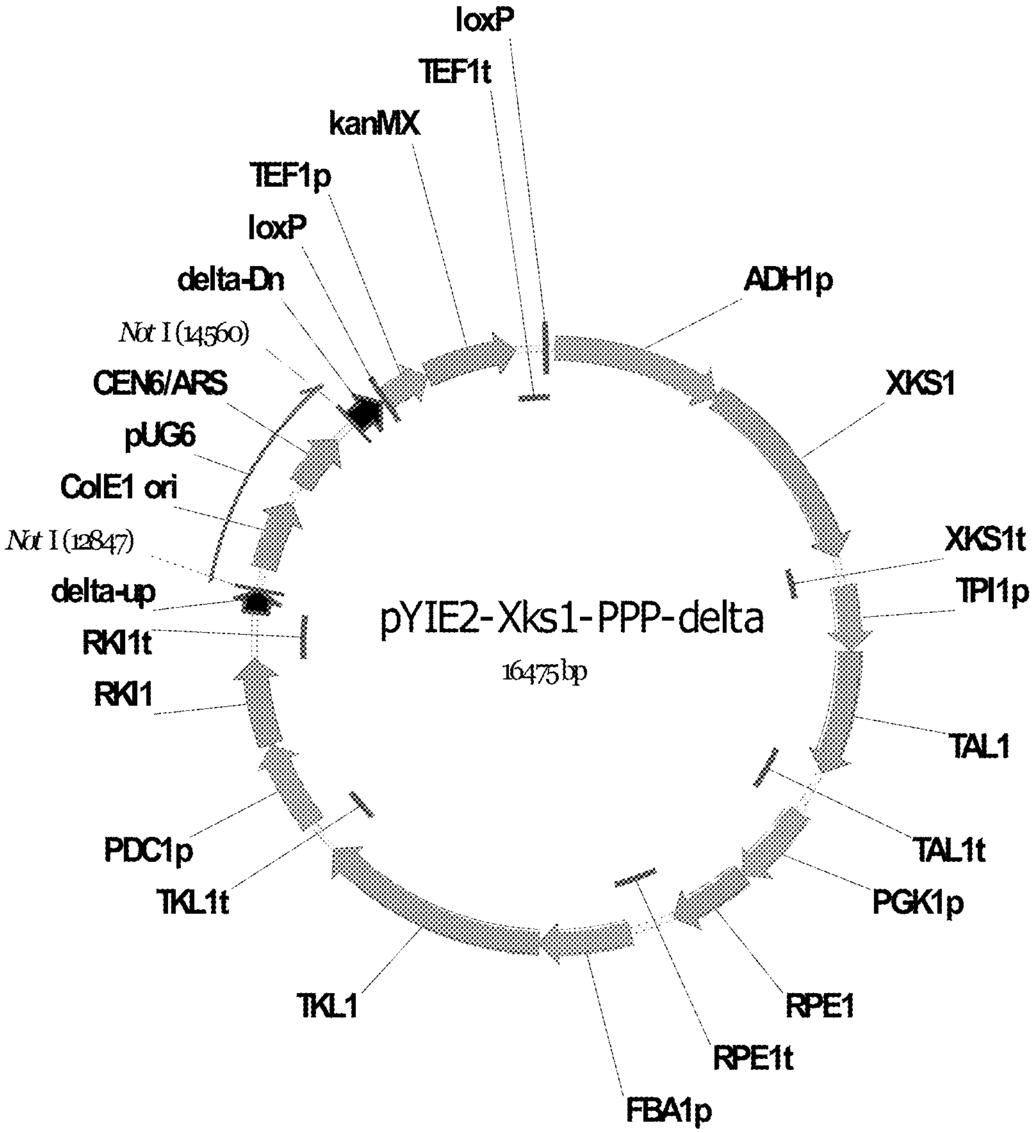
FIG. 3 shows a map of the resulting plasmid pYIE2-XKS1-PPP-δ.

A map of the resulting plasmid pYIE2-XKS1-PPP-δ is shown in FIG. 3. A table listing the genetic elements used is shown below in Table 2.

TABLE 2

| Base position (bp) | Size (bp) | Genetic element | Description | Origion |
|---|---|---|---|---|
| 1-1500 | 1500 | ADH1p | Yeast ADH1 promoter | *Saccharomyces cerevisiae* |
| 1501-3303 | 1803 | XKS1 | Xylulo kinase | *Saccharomyces cerevisiae* |
| 3303-3563 | 260 | XKS1t | Xylulo kinase terminator | *Saccharomyces cerevisiae* |
| 3564-4149 | 586 | TPI 1p | Yeast TPI promoter | *Saccharomyces cerevisiae* |
| 4150-5257 | 1108 | TAL1 | Trans-aldolase | *Saccharomyces cerevisiae* |
| 5258-5657 | 400 | TAL1t | Trans-aldolase terminator | *Saccharomyces cerevisiae* |
| 5658-6407 | 750 | PGK1p | Yeast PGK promoter | *Saccharomyces cerevisiae* |
| 6408-7124 | 717 | RPE1 | Ribulose 5 phosphate epimerase | *Saccharomyces cerevisiae* |
| 7125-7524 | 400 | RPE1t | Ribulose 5 phosphate epimerase terminator | *Saccharomyces cerevisiae* |
| 7525-8344 | 820 | FBA1p | Yeast FBA promoter | *Saccharomyces cerevisiae* |
| 8345-10387 | 2043 | TKL1 | Trans-ketolase | *Saccharomyces cerevisiae* |
| 10387-10667 | 280 | TKL1t | Trans-ketolase terminator | *Saccharomyces cerevisiae* |
| 10668-11467 | 800 | PDC1p | Yeast PDC promoter | *Saccharomyces cerevisiae* |
| 11468-12444 | 777 | RKI1 | Ribose 5 phosphate isomerase | *Saccharomyces cerevisiae* |
| 12445-12644 | 400 | RKI1t | Ribose 5 phosphate isomerase terminator | *Saccharomyces cerevisiae* |
| 12645-12844 | 200 | Delta up | Delta DNA upstream sequence | *Saccharomyces cerevisiae* |
| 12845-14565 | 1720 | pUG6 | *E. coli* vector including ColE1 origin for *E. coli* replication and CEN6/ARS replication origin for yeast replication | *Escherichia coli* |
| 14566-14865 | 300 | Delta Dn | Delta DNA downstream sequence | *Saccharomyces cerevisiae* |
| 14866-14907 | 82 | Linker | Synthetic linker | Synthetic DNA |
| 14908-14941 | 34 | loxP | Lox recombination site | Bacteriophage P1 |
| 14942-15339 | 398 | TEF1p | *A. gossypii* TEF promoter | *Ashbya gossypii* |
| 15340-16149 | 810 | KanMX | Kanamycin (G418) resistance marker | *Escherichia coli* |
| 16150-16414 | 256 | TEF1t | *A. gossypii* TEF terminator. | *Ashbya gossypii* |
| 16415-16448 | 34 | loxP | Lox recombination site | Bacteriophage P1 |
| 16449-16475 | 27 | Linker | Synthetic linker | Synthetic DNA |

The plasmid pYIE2-XKS1-PPP-δ was digested with NotI and the vector elements were removed by agarose gel electrophoresis. The linear fragment containing all of the expression cassettes were then transformed into CIBTS0916 for double homologous recombination followed by selection for kanamycin (G418) resistance. A kanamycin resistant colony was selected and termed CIBTS0931.

CIBTS0931 contains both the zeocin selection marker and the kanamycin selection marker. Both of them are flanked with loxP recombination sites.

In order to remove the zeocin and kanamycin resistance markers the strain was transformed with the episomal plasmid pSH47-hyg again, and transformants were selected on plates containing hygromycin. Subsequently, screening for transformants that had lost zeocin and kanamycin resistance was performed and after that screening for a strain that also lost the hygromycin resistance marker was done. A strain CIBTS1000 was selected and shown to have lost the plasmid pSH47-hyg.

Example 2: Adaptation of the Strain CIBTS1000 to High Xylose Uptake and Acetate Resistance The strain CIBTS1000 was modified so that it could utilize xylose as a carbon source and ferment it to ethanol. However, the xylose utilization was very inefficient. A well-known way to improve that in the field of metabolic engineering is to use adaptation. This was also done in this case. The strain CIBTS1000 was serially transferred from shakeflask to shakeflask in a medium containing xylose as sole carbon source and yeast growth inhibitors known to be present in cellulosic biomass hydrolysates. During these serial transfers mutations are accumulated that enable the strain to grow better under the conditions provided—and thereby to utilize xylose better.

In a first round of adaptation, CIBTS1000 was serially transferred in a shake flask system using YPX medium (10 g/l Yeast extract, 20 g/l peptone and 20 g/l xylose) and YPDX (10 g/l Yeast extract, 20 g/l peptone 10 g/l glucose and 10 g/l xylose)

In a second round of adaptation serial transfer was done in YPXI (YPX supplemented with 43 mM sodium formate, 50 mM sodium acetate and 100 mM sodium sulphate) and YPDXI (YPDX supplemented with 43 mM sodium formate, 50 mM sodium acetate and 100 mM sodium sulphate).

In a final round of adaptation serial transfer was done using NREL dilute acid pretreated corn stover hydrolysate (see Example 3) supplemented with 10 g/l Yeast extract, 20 g/l peptone, 10 g/l glucose and 10 g/l xylose.

A strain named CIBTS1260-J132-F3 was selected as an adapted strain.

Figure 4:
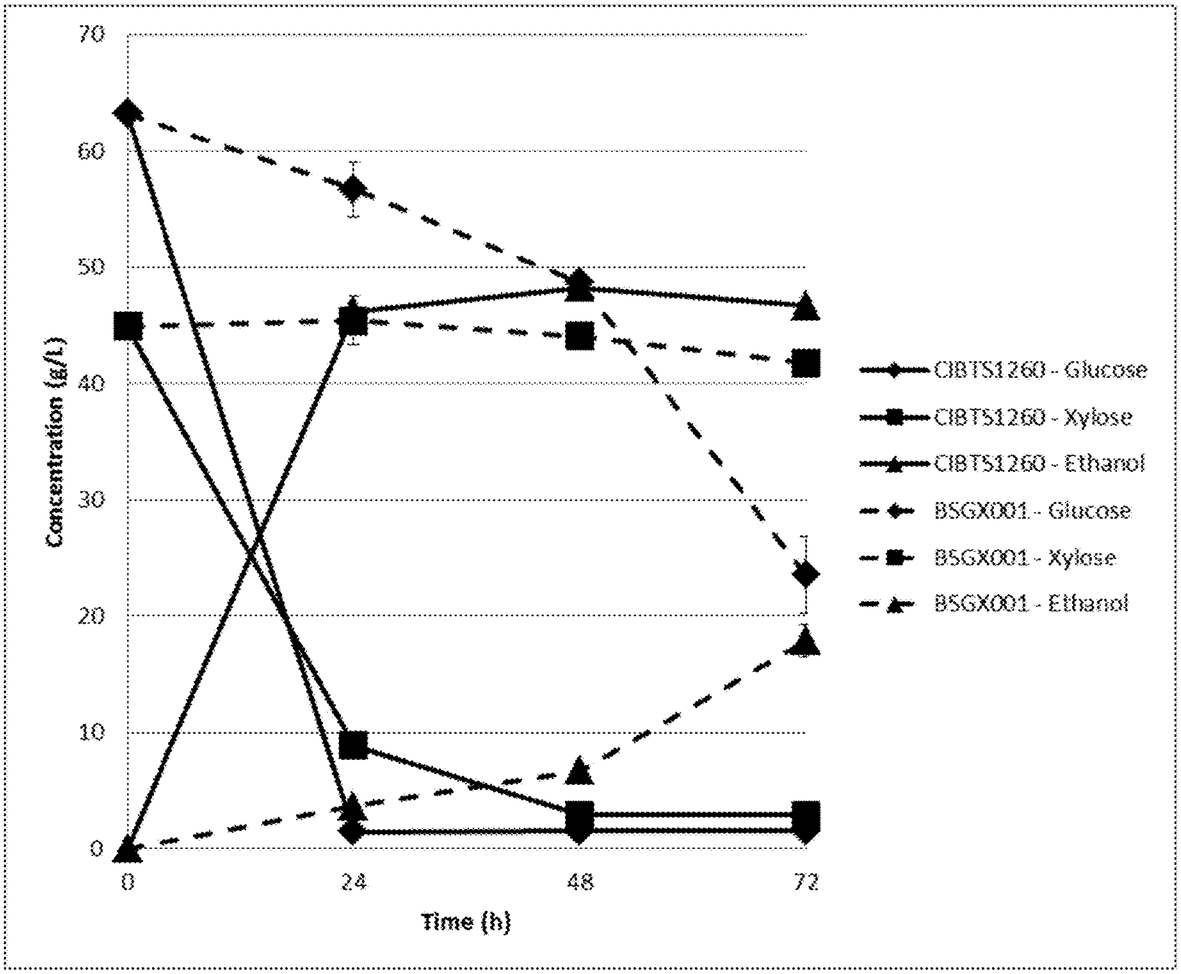
FIG. 4 shows a fermentation comparison of CIBTS1260 versus BSGX001 in NREL Acid Pretreated Corn Stover Hydrolysate at 1 g DCW/L yeast pitch, 35° C., pH 5.5, in 72 hours.

Example 3: Fermentation Comparison of CIBTS1260 and BSGX001 in NREL Dilute Acid Pretreated Corn Stover Hydrolysate Two *Saccharomyces cerevisiae* strains, CIBTS1260 and BSGX001, were tested in NREL dilute acid pretreated corn stover hydrolysate (4% w/w sulfuric acid at 180° C. for 5 minutes). The hydrolysate was produced after 3 days of hydrolysis in a 20 kg reactor at 50° C. with 20 mg enzyme protein/g glucan of Cellulolytic Enzyme Composition CA. The dilute acid pretreated corn stover hydrolysate had a final composition of 63.2 g/L glucose, 44.9 g/L xylose, 0.8 g/L glycerol, and 9.5 g/L acetate. Prior to fermentation, each strain was propagated in a 30° C. air shaker at 150 rpm on YPD medium (10 g/L yeast extract, 20 g/L peptone, and 20 g/L glucose). After 24 hours of growth, these two yeast strains were tested in 50 ml of hydrolysate in 125 ml baffled Erlenmeyer flasks at a yeast pitch of 1 g dry cell weight (DCW)/L. Rubber stoppers equipped with 18 gauge blunt fill needles were used to seal each flask, and the flasks were placed in a 35° C. air shaker at a speed of 150 rpm. Samples were taken at 24, 48, and 72 hours for determination of glucose, xylose, and ethanol concentrations via HPLC analysis. The results were averaged for each set of 3 replicates, and are given in FIG. 1 which shows a comparison of CIBTS1260 versus BSGX001 in NREL acid pretreated corn stover hydrolysate at 1 g/L yeast pitch in 72 hours. As shown in FIG. 4, by 48 hours, the CIBTS1260 strain completed full xylose consumption and produced approximately 47 g/L ethanol. The BSGX001 strain, however, was slow to uptake glucose for ethanol conversion and thus consumed only 3 g/L xylose. These results indicate that CIBTS1260 results in improved xylose uptake and utilization for conversion to ethanol compared to BSGX001.

Example 4: Comparison of CIBTS1260 and BSGX001 for Fermentation Performance in Model Media The fermentation performance of CIBTS1260 and its precursor BSGX001 was compared. Prior to fermentation, each strain was propagated in a 30° C. air shaker at 150 rpm on YPD medium (10 g/L yeast extract, 20 g/L peptone, and 20 g/L glucose). After 24 hours of growth, these two yeast strains were tested in YPX medium (5 g/L yeast extract, 5 g/L peptone, and 50 g/L xylose). To test fermentation performance, each strain was inoculated into 50 ml of YPX medium in 125 ml baffled Erlenmeyer flasks at a yeast pitch of 2 g DCW/L. Rubber stoppers equipped with 18 gauge blunt fill needles were used to seal each flask, and the flasks were placed in a 32° C. air shaker at a speed of 150 rpm. Samples were taken at 24, 48, and 72 hours for determination of glucose, xylose, and ethanol concentrations via HPLC analysis. The results were averaged for each set of 3 replicates, and are given in FIG. 5.

Figure 5:
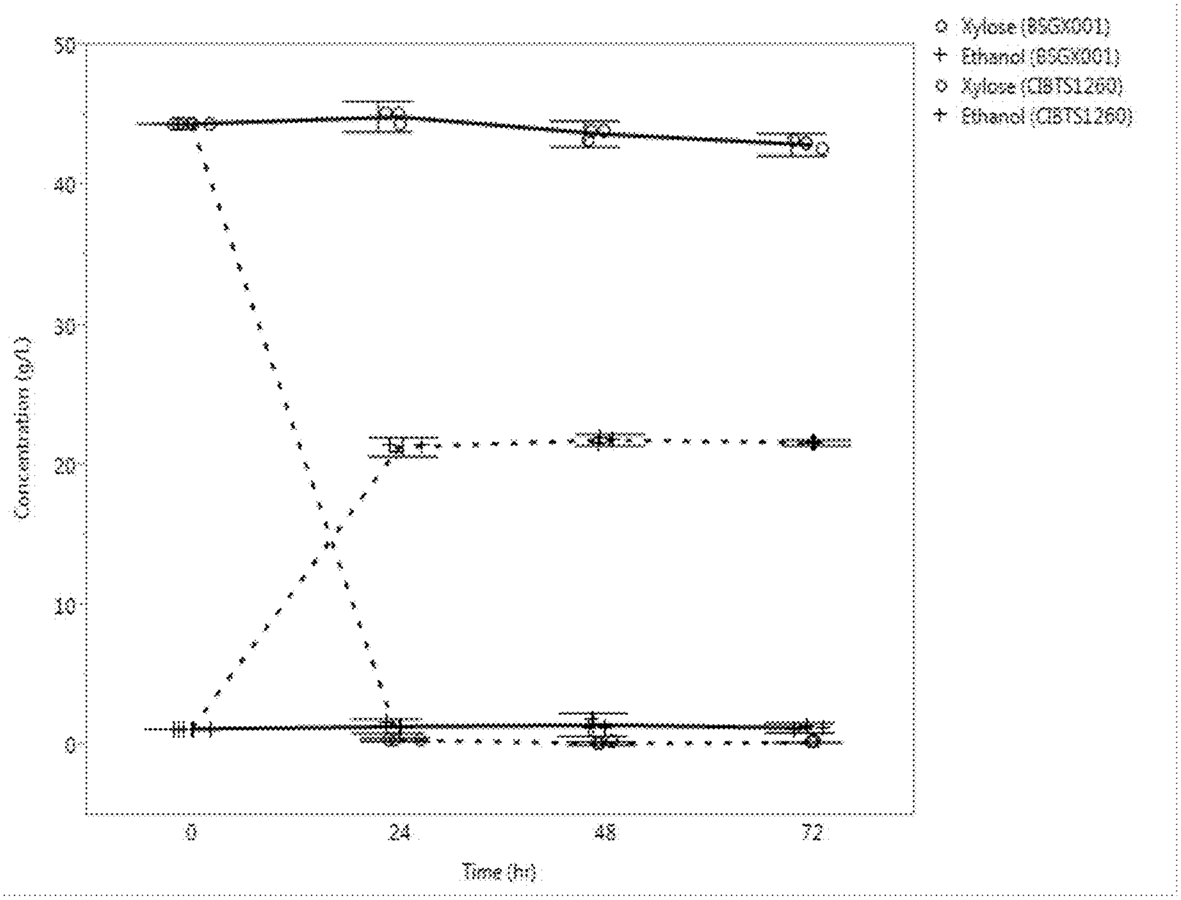
FIG. 5 shows a comparison of CIBTS1260 vs. BSGX001 in model media: 2/L yeast pitch, 32° C., pH 5.5, 72 hours.

As shown in FIG. 5, CIBTS1260 (dotted lines) has completely utilized all available xylose in 24 hours and produced 21.3 g/L of ethanol. In the 72 hour fermentation time, BSGX001 (solid lines) consumed 1.5 g/L of xylose, and the resulting ethanol concentration was 1.3 g/L.

Example 5: Fermentation of Cellulolytic Enzyme Composition CA ("CA") and Cellulolytic Enzyme Composition CB ("CB") Bagasse Hydrolysate with CIBTS1260

CIBTS1260 was used in fermentation tests with NREL dilute acid pretreated bagasse hydrolysates generated at Novozymes North America, USA. The hydrolysate was produced after 5 days of hydrolysis in 2 L IKA reactors at 50° C. with a 6 mg enzyme protein/g glucan dose of two cellulolytic enzyme compositions termed "CA" and "CB". These materials are representative benchmarks for dilute acid pretreated bagasse hydrolysates with final compositions of 40.7 and 58.7 g/L glucose, 42.5 and 44.7 g/L xylose, 0.19 and 0.08 g/L glycerol, and 8.99 and 11.3 g/L acetate for "CA" and "CB", respectively. Prior to fermentation, the yeast were propagated in a 30° C. air shaker at 150 rpm on 2% YPD medium (10 g/L yeast extract, 20 g/L peptone, and 20 g/L glucose). After 24 hours of growth, CIBTS1260 was tested in 50 ml of "CA" and "CB" hydrolysate in 125 ml baffled Erlenmeyer flasks at a yeast pitch of 1 g DCW/L.

Figure 6:
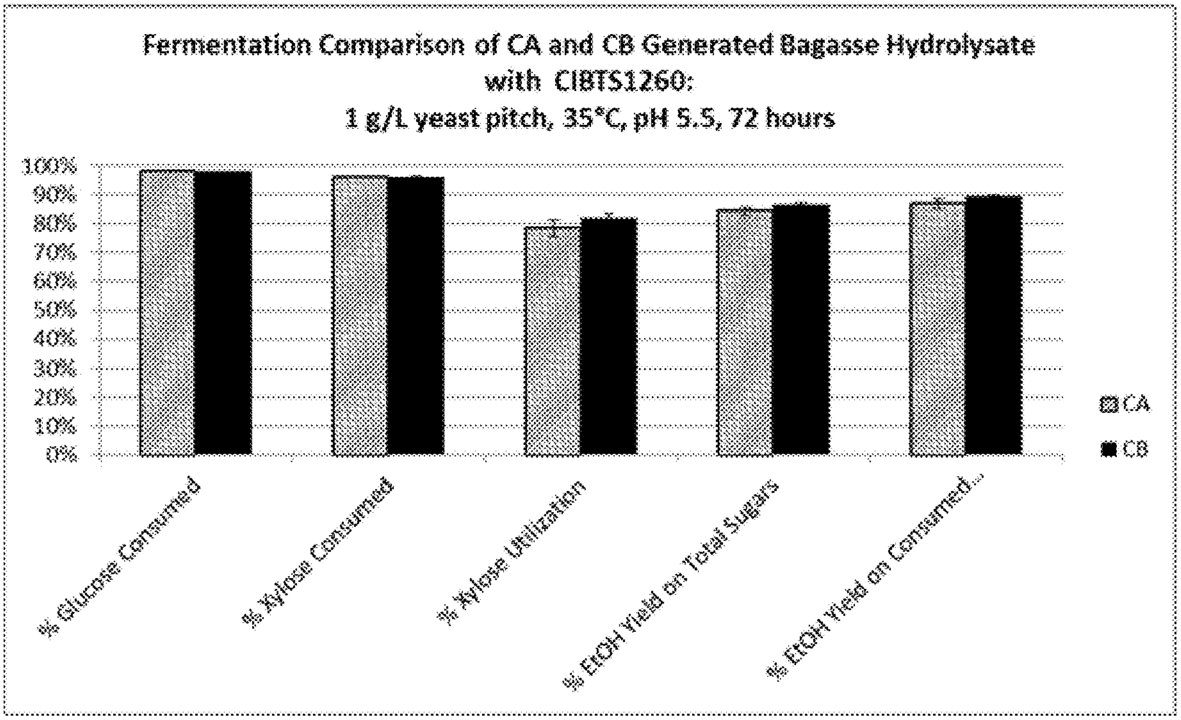
FIG. 6 shows a fermentation comparison of Cellulolytic Enzyme Composition CA and Cellulolytic Enzyme Composition CB generated bagasse hydrolysate with CIBTS1260 at 1 g/L yeast pitch in 72 hours.

Rubber stoppers equipped with 18 gauge blunt fill needles were used to seal each flask, and the flasks were placed in a 35° C. air shaker at a speed of 150 rpm. Samples were taken at 24, 48, and 72 hours for determination of glucose, xylose, ethanol, acetate, and glycerol concentrations via HPLC analysis. The results were averaged for each set of 3 replicates, and are given in FIG. 6. Greater than 95% of the glucose and xylose present in both systems was consumed within the 72 hour time period with ethanol yields on total sugars of 84.1% for the "CA" hydrolysate and 86.4% for the "CB" hydrolysate.

Figure 7:
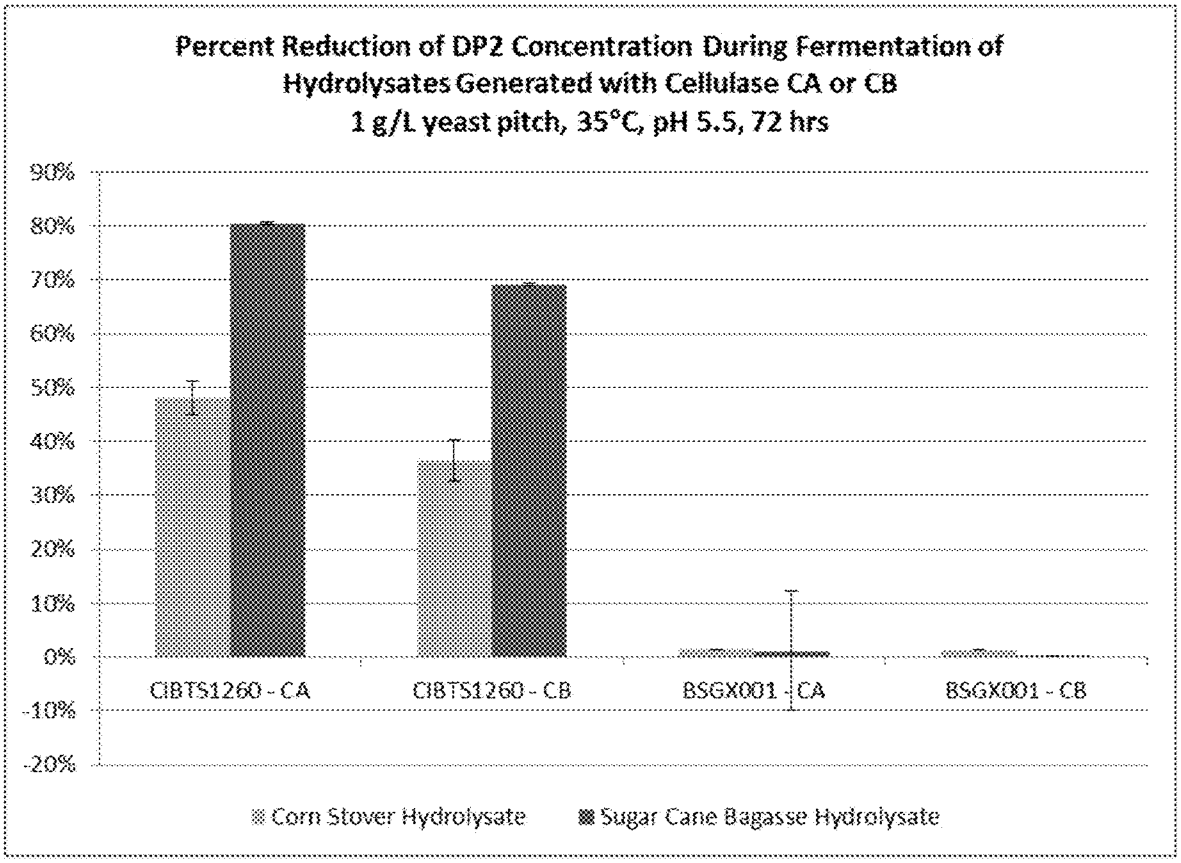
FIG. 7 shows percentage reduction of DP2 concentration during fermentation of hydrolysates generated with Cellulase CA or CB at 1 g/L yeast pitch, 35° C., pH 5.5, 72 hours.

Example 6: DP2 Reduction During CIBTS1260 and BSGX001 Fermentations of Dilute Acid Pretreated Corn Stover and Sugar Cane Bagasse Hydrolysates Dilute acid pretreated corn stover and sugar cane bagasse from National Renewable Energy Laboratory (NREL), USA, were hydrolysed with a 6 mg enzyme protein/g glucan dose of two enzyme product cocktails termed CA and CB for 5 days in 2 L IKA reactors at 50° C. Prior to fermentation, the CIBTS1260 and BSGX001 yeast were propagated in a 30° C. air shaker at 150 rpm on YPD medium (10 g/L yeast extract, 20 g/L peptone, and 20 g/L glucose). After 24 hours of growth, the cells from each strain were harvested via centrifugation and added to 50 ml of CA and CB hydrolysate supplemented with 2 g/L urea in 125 ml baffled Erlenmeyer flasks at a yeast pitch of 1 g DCW/L (Dry Cell Weight/L), respectively. Rubber stoppers equipped with 18 gauge blunt fill needles were used to seal each flask, and the flasks were placed in a 35° C. air shaker at a speed of 150 rpm. Samples were taken at 0 and 72 hours for determination DP2 concentrations via HPLC analysis. The results were averaged for each set of replicates (n=3 for CIBTS1260 and n=2 for BSGX001). As shown in FIG. 7, in the same hydrolysates, the DP2 concentrations were reduced more for fermentations conducted with CIBTS1260 than for fermentations with BSGX001. The DP2 peak, as measured on HPLC, contains cellobiose and short chain sugars.

Example 7: Fermentation Comparison of Strains MBG5147-MBG5151 with CIBTS1260

*Saccharomyces cerevisiae* Strains CIBTS1260, MBG5147, MBG5148, MBG5149, MBG5150 and MBG5151 were cultivated from slant tubs onto PDA plates at 32° C. for 24 to 48 h. Isolated colonies were grown in YPD media in shake flasks at 32° C. for 24 h and aliquots stocked in 2 mL cryovial containing 20% glycerol at −80° C. ultrafreezer.

The cell propagation for fermentation was carried out in two steps in 500 mL baffled flasks, containing 100 mL media, incubated in a shaker at 32° C., 150 rpm. The first step culture media was inoculated with 1 cryovial and after 16 h, then transferred to second flask. At the end of incubation, cell growth was measured by DO at 600 nm in spectrophotometer and converted to Dry Weight Cell in g/L.

Fermentation were conducted using a C5-liquor obtained from pretreated sugar cane bagasse in 250 mL Schott flask containing 50 mL media, pH 5.5, inoculated with propagation media and incubated at 32° C., 110 rpm in an orbital incubator. For inoculation, the media concentration was adjusted to account for different growth rate in order to start the fermentation with the same cell pitch (1 g/L). The kinetic of fermentations were monitored by ANKOM RF Gas Production System and after 48 h fermentation, samples were taken and analyzed for sugars, ethanol, glycerol and acetic acid by HPLC (columns HPX87-H, RID detector) and xylose by Xylose Enzymatic Kit (Megazyme).

Figure 8:
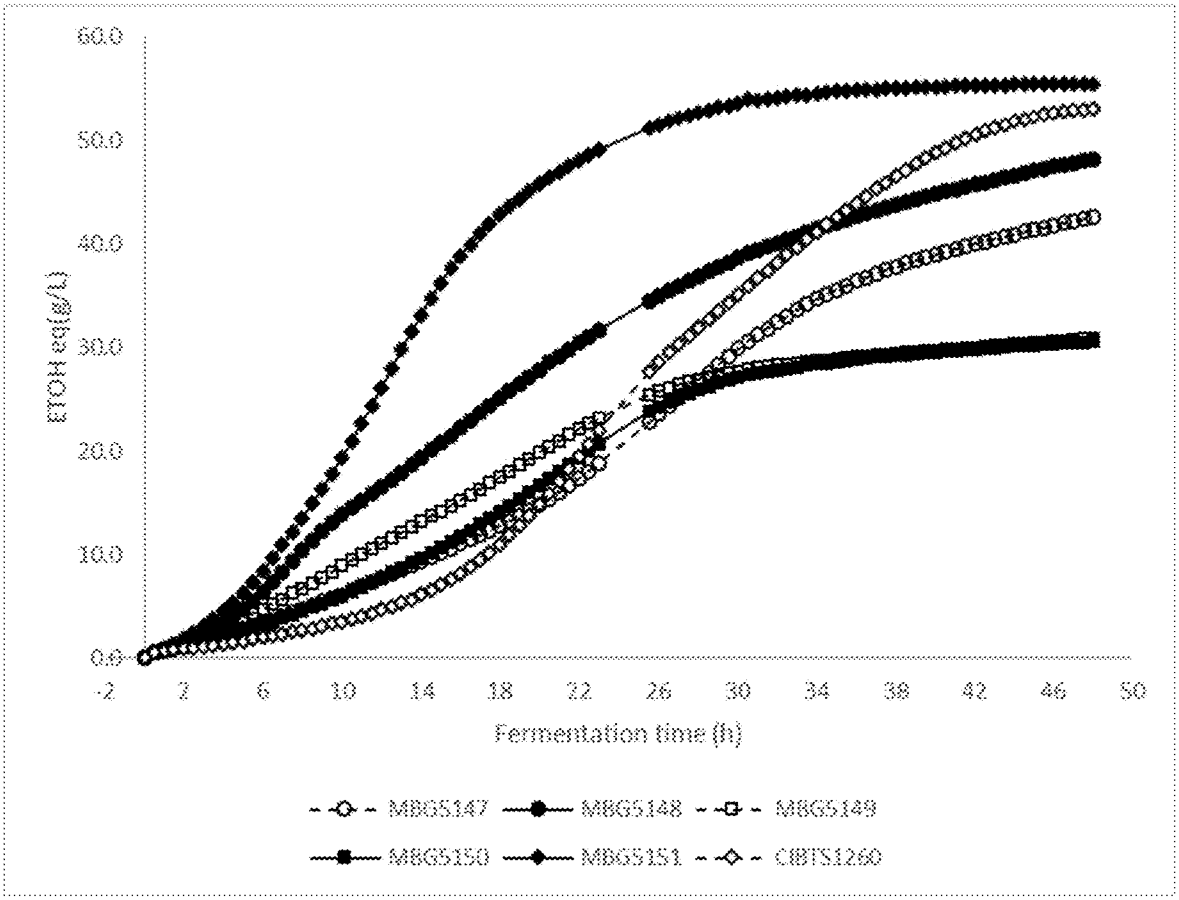
FIG. 8 shows a kinetic profile for fermentations of MBG5147-MBG5151 vs. CIBTS1260.

FIG. 8 shows the kinetic profile for fermentations of MBG5147-MBG5151 vs. CIBTS1260 based on gas pressure monitoring and converted to gas mass according to calculations ANKOM RF Gas Production System. Table 3 shows residual sugars, ethanol titer, ethanol yields, and consumbed xylose. The data shows that MBG5151 has a faster fermentation rate compared to the remaining strains tested, including CIBTS1260.

TABLE 3

| Strains | TRS from Must + Prop (g/L) | Residual Xylose (g/L) | Ethanol (g/L) | Yield (g/g) | Yield (%) | % Xylose consumed |
|---|---|---|---|---|---|---|
| MBG 5147 (A) | 125.93 | n.a. | 42.97 | 0.336 | 65.67% | n.a. |
| MBG 5147 (B) | 125.93 | n.a. | 44.80 | 0.350 | 68.52% | n.a. |
| MBG 5148 (A) | 120.16 | 9.564 | 52.08 | 0.410 | 80.17% | 84.80% |
| MBG 5148 (B) | 120.16 | 9.444 | 51.46 | 0.405 | 79.17% | 84.99% |
| MBG 5149 (A) | 123.20 | n.a. | 35.77 | 0.276 | 54.10% | n.a. |
| MBG 5149 (B) | 123.20 | n.a. | 33.98 | 0.262 | 51.25% | n.a. |
| MBG 5150 (A) | 126.48 | n.a. | 32.72 | 0.254 | 49.62% | n.a. |
| MBG 5150 (B) | 126.48 | n.a. | 32.26 | 0.250 | 48.91% | n.a. |
| MBG 5151 (A) | 125.98 | 0.242 | 58.00 | 0.454 | 88.91% | 99.62% |
| MBG 5151 (B) | 125.98 | 0.343 | 58.39 | 0.457 | 89.52% | 99.46% |
| CIBTS1260 (A) | 119.46 | 0.811 | 57.36 | 0.455 | 88.98% | 98.71% |
| CIBTS1260 (B) | 119.46 | 0.843 | 56.87 | 0.451 | 88.18% | 98.66% |

The invention may further be described in the following numbered paragraphs:

Paragraph [1]. A method of producing a fermentation product from a cellulosic-containing and/or starch-containing material, the method comprising:

(a) saccharifying the cellulosic-containing or starch-containing material; and (b) fermenting the saccharified material of step (a) with a fermenting organism under suitable conditions to produce the fermentation product; wherein the fermenting organism is a recombinant strain of *Saccharomyces cerevisiae* deposited under the Budapest Treaty at the Agricultural Research Service Patent Culture Collection (NRRL) having deposit accession no. NRRL Y-67971 (*Saccharomyces cerevisiae* strain MBG5151), or a derivative thereof (e.g., expressing a heterologous polypeptide such as a glucoamylase and/or alpha-amylase) or a fermenting organism having properties that are about the same as that of *Saccharomyces cerevisiae* MBG5151.

Paragraph [2]. A method of producing a fermentation product from a cellulosic-containing and/or starch-containing material, the method comprising:

(a) saccharifying the cellulosic-containing or starch-containing material; and (b) fermenting the saccharified material of step (a) with a fermenting organism under suitable conditions to produce the fermentation product; wherein the fermenting organism is a recombinant strain of *Saccharomyces cerevisiae* deposited under the Budapest Treaty at the Agricultural Research Service Patent Culture Collection (NRRL) having deposit accession no. NRRL Y-68015 (*Saccharomyces cerevisiae* strain MBG5248), or a derivative thereof (e.g., expressing a heterologous polypeptide such as a glucoamylase and/or alpha-amylase) or a fermenting organism having properties that are about the same as that of *Saccharomyces cerevisiae* MBG5248.

Paragraph [3]. The method of paragraph [1] or [2], comprising recovering the fermentation product from the fermentation.

Paragraph [4]. The method of paragraph [3], wherein recovering the fermentation product from the fermentation comprises distillation.

Paragraph [5]. The method of any one of paragraphs [1]-[4], wherein fermentation and saccharification are performed simultaneously in a simultaneous saccharification and fermentation (SSF).

Paragraph [6]. The method of any one of paragraphs [1]-[4], wherein fermentation and saccharification are performed sequentially (SHF).

Paragraph [7]. The method of any one of paragraphs [1]-[6], wherein the fermentation product is ethanol.

Paragraph [8]. The method of any one of paragraphs [1]-[7], wherein step (a) comprises contacting the starch-containing and/or cellulosic-containing material with an enzyme composition.

Paragraph [9]. The method of any one of paragraphs [1]-[7], wherein step (a) comprises saccharifying a cellulosic-containing material.

Paragraph [10]. The method of paragraph [9], wherein the cellulosic-containing material is pretreated.

Paragraph [11]. The method of any of paragraphs [9] or [10], wherein the cellulosic-containing material comprises bagasse.

Paragraph [12]. The method of any of paragraphs [9]-[11], wherein step (a) comprises contacting the cellulosic-containing material with an enzyme composition, and wherein the enzyme composition comprises one or more enzymes selected from a cellulase, an AA9 polypeptide, a hemicellulase, a CIP, an esterase, an expansin, a ligninolytic enzyme, an oxidoreductase, a pectinase, a protease, and a swollenin.

Paragraph [13]. The method of paragraph [12], wherein the cellulase is one or more enzymes selected from an endoglucanase, a cellobiohydrolase, and a beta-glucosidase.

Paragraph [14]. The method of paragraph [12] or [13], wherein the hemicellulase is one or more enzymes selected a xylanase, an acetylxylan esterase, a feruloyl esterase, an arabinofuranosidase, a xylosidase, and a glucuronidase.

Paragraph [15]. The method of any one of paragraphs [1]-[14], wherein the method results in at least 0.25% (e.g., 0.5%, 0.75%, 1.0%, 1.25%, 1.5%, 1.75%, 2%, 3% or 5%) yield of fermentation product.

Paragraph [16]. The method of any one of paragraphs [1]-[15], wherein fermentation is conducted under low oxygen (e.g., anaerobic) conditions.

Paragraph [17]. The method of any of paragraphs [1]-[16], wherein fermenting organism has one or more of the following properties:

higher ethanol fermentation kinetics compared to *Saccharomyces cerevisiae* CIBTS1260 (e.g., between 10 and 32 hours) at 1 g DWC/L, 32° C., pH 5.5 (as described in Example 7 herein);

higher xylose consumption compared to *Saccharomyces cerevisiae* CIBTS1260 after 48 hours fermentation at 1 g DWC/L, 35° C., pH 5.5 (as described in Example 3 herein);

higher glucose consumption compared to *Saccharomyces cerevisiae* CIBTS1260 after 48 hours fermentation at 1 g DWC/L, 35° C., pH 5.5 (as described in Example 3 herein).

Paragraph [18]. A recombinant *Saccharomyces cerevisiae* strain deposited under the Budapest Treaty at the Agricultural Research Service Patent Culture Collection (NRRL) having deposit accession no. NRRL Y-67971 (*Saccharomyces cerevisiae* strain MBG5151), or a derivative thereof (e.g., expressing a heterologous polypeptide such as a glucoamylase and/or alpha-amylase) or a fermenting organism having properties that are about the same as that of *Saccharomyces cerevisiae* MBG5151.

Paragraph [19]. A recombinant *Saccharomyces cerevisiae* strain deposited under the Budapest Treaty at the Agricultural Research Service Patent Culture Collection (NRRL) having deposit accession no. NRRL Y-68015 (*Saccharomyces cerevisiae* strain MBG5248), or a derivative thereof (e.g., expressing a heterologous polypeptide such as a glucoamylase and/or alpha-amylase) or a fermenting organism having properties that are about the same as that of *Saccharomyces cerevisiae* MBG5248.

Paragraph [20]. The recombinant *Saccharomyces cerevisiae* strain of paragraph [18] or [19], wherein the strain has one or more of the following properties:

higher ethanol fermentation kinetics compared to *Saccharomyces cerevisiae* CIBTS1260 (e.g., between 10 and 32 hours) at 1 g DWC/L, 32° C., pH 5.5 (as described in the Example 7 herein);

higher xylose consumption compared to *Saccharomyces cerevisiae* CIBTS1260 after 48 hours fermentation at 1 g DWC/L, 35° C., pH 5.5 (as described in Example 3 herein);

higher glucose consumption compared to *Saccharomyces cerevisiae* CIBTS1260 after 48 hours fermentation at 1 g DWC/L, 35° C., pH 5.5 (as described in Example 3 herein).

Paragraph [21]. The recombinant *Saccharomyces cerevisiae* strain of any one of paragraphs [18]-[20], wherein the strain is capable of higher ethanol yield compared to *Saccharomyces cerevisiae* CIBTS1260 at 1 g DWC/L, 32° C., pH 5.5 (as described in Example 7 herein) between 10 to 30 hours of fermentation.

Paragraph [22]. The recombinant *Saccharomyces cerevisiae* strain of any of paragraphs [18]-[21], wherein the strain is capable of greater than 95% xylose consumption by 48 hours fermentation under the process conditions of 1 g DCW/L, 35° C., pH 5.5 (as described in Example 3 herein).

Paragraph [23]. The recombinant *Saccharomyces cerevisiae* strain of any of paragraphs [18]-[22], wherein the strain is capable of greater than 95% glucose consumption by 24 hours fermentation under the process conditions of 1 g DCW/L, 35° C., pH 5.5 (as described in Example 3 herein).

Paragraph [24]. The recombinant *Saccharomyces cerevisiae* of any of paragraphs [18]-[23], wherein the strain is capable of providing more than 30 g/L ethanol, such as more than 40 g/L ethanol, such as more than 45 g/L ethanol, such as approximately 47 g/L ethanol after 48 hours fermentation under the process conditions of 1 g DCW/L, 35° C., pH 5.5 (as described in Example 3 of herein).

Paragraph [25]. The recombinant *Saccharomyces cerevisiae* of any of paragraphs [18]-[24], comprising a heterologous gene encoding a xylose isomerase.

Paragraph [26]. The recombinant *Saccharomyces cerevisiae* of any of paragraphs [18]-[25], comprising a heterologous gene encoding a pentose transporter.

Paragraph [27]. The recombinant *Saccharomyces cerevisiae* of any of paragraphs [18]-[26], wherein the pentose transporter gene is a GFX gene, (e.g., GFX1 from *Candida intermedia*).

Paragraph [28]. The recombinant *Saccharomyces cerevisiae* of any of paragraphs [18]-[27], comprising a heterologous gene encoding a xylulokinase (XKS) (e.g., a XKS from *Saccharomyces cerevisiae*).

Paragraph [29]. The recombinant *Saccharomyces cerevisiae* of any of paragraphs [18]-[28], comprising a heterologous gene encoding a ribulose 5 phosphate 3-epimerase (RPE1) (e.g., a RPE1 from *Saccharomyces cerevisiae*).

Paragraph [30]. The recombinant *Saccharomyces cerevisiae* of any of paragraphs [18]-[29], comprising a heterologous gene encoding a ribulose 5 phosphate isomerase (RKI1) (e.g., a RKI1 from *Saccharomyces cerevisiae*).

Paragraph [31]. The recombinant *Saccharomyces cerevisiae* of any of paragraphs [18]-[30], comprising a heterologous gene encoding a transketolase (TKL1) and a heterologous gene encoding a transaldolase (TAL1) (e.g., a TKL1 and TAL1 from *Saccharomyces cerevisiae*).

Paragraph [32]. A method of producing a derivative of *Saccharomyces cerevisiae* strain MBG5151 (deposited under Accession No. NRRL Y-67971 at the Agricultural Research Service Patent Culture Collection (NRRL)), comprising:

a. culturing a first yeast strain with a second yeast strain, wherein the second yeast strain is *Saccharomyces cerevisiae* strain MBG5151 or a derivative thereof, under conditions which permit combining of DNA between the first yeast strain and the second yeast strain; and
b. isolating hybrid strains; and
c. optionally repeating steps (a) and (b) using a hybrid strain isolated in step (b) as the first yeast strain and/or the second yeast strain.

Paragraph [33]. A method of producing a derivative of *Saccharomyces cerevisiae* strain MBG5248 (deposited under Accession No. NRRL Y-68015 at the Agricultural Research Service Patent Culture Collection (NRRL)), comprising:

a. culturing a first yeast strain with a second yeast strain, wherein the second yeast strain is *Saccharomyces cerevisiae* strain MBG5248 or a derivative thereof, under conditions which permit combining of DNA between the first yeast strain and the second yeast strain; and
b. isolating hybrid strains; and
c. optionally repeating steps (a) and (b) using a hybrid strain isolated in step (b) as the first yeast strain and/or the second yeast strain.

Paragraph [34]. A method of producing a derivative of *Saccharomyces cerevisiae* strain MBG5151 (deposited under Accession No. NRRL Y-67971 at the Agricultural Research Service Patent Culture Collection (NRRL)) which exhibits the defining characteristics of *Saccharomyces cerevisiae* strain MBG5151, comprising:

(a) providing:
  (i) a first yeast strain; and
  (ii) a second yeast strain, wherein the second yeast strain is *Saccharomyces cerevisiae* strain MBG5151 or a derivative thereof;
(b) culturing the first yeast strain and the second yeast strain under conditions which permit combining of DNA between the first and second yeast strains;
(c) screening or selecting for a derivative of *Saccharomyces cerevisiae* strain MBG5151.

Paragraph [35]. The method of paragraph [34], wherein step (c) comprises screening or selecting for a hybrid strain which exhibits one or more defining characteristic of *Saccharomyces cerevisiae* strain MBG5151.

Paragraph [36]. The method of paragraph [34], comprising the further step of:

(d) repeating steps (a) and (b) with the screened or selected strain from step (c) as the first and/or second strain, until a derivative is obtained which exhibits the defining characteristics of *Saccharomyces cerevisiae* strain MBG5151.

Paragraph [37]. The method of paragraph [34], wherein the culturing step (b) comprises:

(i) sporulating the first yeast strain and the second yeast strain;
(ii) hybridizing germinated spores produced by the first yeast strain with germinated spores produced by the second yeast strain.

Paragraph [38]. A method of producing a derivative of *Saccharomyces cerevisiae* strain MBG5248 (deposited under Accession No. NRRL Y-68015 at the Agricultural Research Service Patent Culture Collection (NRRL)) which exhibits the defining characteristics of *Saccharomyces cerevisiae* strain MBG5248, comprising:

(d) providing:
  (j) a first yeast strain; and
  (iii) a second yeast strain, wherein the second yeast strain is *Saccharomyces cerevisiae* strain MBG5248 or a derivative thereof;
(e) culturing the first yeast strain and the second yeast strain under conditions which permit combining of DNA between the first and second yeast strains;
(f) screening or selecting for a derivative of *Saccharomyces cerevisiae* strain MBG5248.

Paragraph [39]. The method of paragraph [38], wherein step (c) comprises screening or selecting for a hybrid strain which exhibits one or more defining characteristic of *Saccharomyces cerevisiae* strain MBG5248.

Paragraph [40]. The method of paragraph [38], comprising the further step of:

(d) repeating steps (a) and (b) with the screened or selected strain from step (c) as the first and/or second strain, until a derivative is obtained which exhibits the defining characteristics of *Saccharomyces cerevisiae* strain MBG5248.

Paragraph [41]. The method of paragraph [38], wherein the culturing step (b) comprises:

(i) sporulating the first yeast strain and the second yeast strain;
(ii) hybridizing germinated spores produced by the first yeast strain with germinated spores produced by the second yeast strain.

Paragraph [42]. A method of producing a recombinant derivative of *Saccharomyces cerevisiae* strain MBG5151 (deposited under Accession No. NRRL Y-67971 at the Agricultural Research Service Patent Culture Collection (NRRL)) comprising:

(a) transforming *Saccharomyces cerevisiae* strain MBG5151 (or a derivative of *Saccharomyces cerevi-*

*siae* strain MBG5151) with one or more expression vectors (e.g., one or more expression vectors encoding a glucoamylase and/or an alpha-amylase); and (b) isolating the transformed strain.

Paragraph [43]. A method of producing a recombinant derivative of *Saccharomyces cerevisiae* strain MBG5248 (deposited under Accession No. NRRL Y-68015 at the Agricultural Research Service Patent Culture Collection (NRRL)) comprising:

(a) transforming *Saccharomyces cerevisiae* strain MBG5248 (or a derivative of *Saccharomyces cerevisiae* strain MBG5248) with one or more expression vectors (e.g., one or more expression vectors encoding a glucoamylase and/or an alpha-amylase); and (b) isolating the transformed strain.

Paragraph [44]. A *Saccharomyces cerevisiae* strain produced by the method of any one of paragraphs [32]-[43].

Paragraph [45]. A method of producing ethanol, comprising incubating a *Saccharomyces cerevisiae* strain of any of paragraphs [18]-[31] and [44] with a substrate comprising a fermentable sugar under conditions which permit fermentation of the fermentable sugar to produce ethanol.

Paragraph [46]. Use of a *Saccharomyces cerevisiae* strain of any of paragraphs [18]-[31] and [44] in the production of ethanol.

Paragraph [47]. Use of a *Saccharomyces cerevisiae* strain of any of paragraph [18], [20]-[31] and [44] in the production of a *Saccharomyces* strain having the defining characteristics of *Saccharomyces cerevisiae* strain MBG5151 (deposited under Accession No. NRRL Y-67971 at the Agricultural Research Service Patent Culture Collection (NRRL), Northern Regional Research Center, 1815 University Street, Peoria, IL, USA).

Paragraph [48]. Use of a *Saccharomyces cerevisiae* strain of any of paragraph [19]-[31] and [44] in the production of a *Saccharomyces* strain having the defining characteristics of *Saccharomyces cerevisiae* strain MBG5248 (deposited under Accession No. NRRL Y-68015 at the Agricultural Research Service Patent Culture Collection (NRRL), Northern Regional Research Center, 1815 University Street, Peoria, IL, USA).

Paragraph [49]. Use of *Saccharomyces cerevisiae* strain MBG5151 (deposited under Accession No. NRRL Y-67971 at the Agricultural Research Service Patent Culture Collection (NRRL), Northern Regional Research Center, 1815 University Street, Peoria, IL, USA) in the production of a *Saccharomyces* strain having properties that are about the same as that of *Saccharomyces cerevisiae* strain MBG5151 or which exhibits one or more defining characteristics of *Saccharomyces cerevisiae* strain MBG5151.

Paragraph [50]. Use of *Saccharomyces cerevisiae* strain MBG5248 (deposited under Accession No. NRRL Y-68015 at the Agricultural Research Service Patent Culture Collection (NRRL), Northern Regional Research Center, 1815 University Street, Peoria, IL, USA) in the production of a *Saccharomyces* strain having properties that are about the same as that of *Saccharomyces cerevisiae* strain MBG5248 or which exhibits one or more defining characteristics of *Saccharomyces cerevisiae* strain MBG5248.

Paragraph [51]. Use of *Saccharomyces cerevisiae* strain MBG5151 (deposited under Accession No. NRRL Y-67971 at the Agricultural Research Service Patent Culture Collection (NRRL), Northern Regional Research Center, 1815 University Street, Peoria, IL, USA) or a strain having properties that are about the same as that of *Saccharomyces cerevisiae* strain MBG5151 or a derivative thereof in a method according to any of paragraphs [1]-[17].

Paragraph [52]. Use of *Saccharomyces cerevisiae* strain MBG5248 (deposited under Accession No. NRRL Y-68015 at the Agricultural Research Service Patent Culture Collection (NRRL), Northern Regional Research Center, 1815 University Street, Peoria, IL, USA) or a strain having properties that are about the same as that of *Saccharomyces cerevisiae* strain MBG5248 or a derivative thereof in a method according to any of paragraphs [2]-[16].

Paragraph [53]. A composition comprising a *Saccharomyces cerevisiae* strain of any of paragraphs [18]-[31] and [44], and one or more naturally occurring and/or non-naturally occurring components.

Paragraph [54]. The composition of paragraph [53], wherein the components are selected from the group consisting of: surfactants, emulsifiers, gums, swelling agents, and antioxidants.

Paragraph [55]. The composition of paragraph [53] or [54], wherein the *Saccharomyces cerevisiae* strain is *Saccharomyces cerevisiae* strain MBG5151 (deposited under Accession No. NRRL Y-67971 at the Agricultural Research Service Patent Culture Collection (NRRL), Northern Regional Research Center, 1815 University Street, Peoria, IL, USA).

Paragraph [56]. The composition of paragraph [53] or [54], wherein the *Saccharomyces cerevisiae* strain is *Saccharomyces cerevisiae* strain MBG5248 (deposited under Accession No. NRRL Y-68015 at the Agricultural Research Service Patent Culture Collection (NRRL), Northern Regional Research Center, 1815 University Street, Peoria, IL, USA).

Paragraph [57]. The composition of any of paragraphs [53]-[56], wherein the *Saccharomyces cerevisiae* strain is in a viable form, in particular in dry, cream or compressed form.

The invention claimed is:

1. A method of producing a fermentation product from a cellulosic-containing and/or starch-containing material, the method comprising:

(a) saccharifying the cellulosic-containing or starch-containing material; and (b) fermenting the saccharified material of step (a) with a fermenting organism under suitable conditions to produce the fermentation product;

wherein the fermenting organism is:

(1) a recombinant strain of *Saccharomyces cerevisiae* deposited under the Budapest Treaty at the Agricultural Research Service Patent Culture Collection (NRRL) having deposit accession no. NRRL Y-67971 (*Saccharomyces cerevisiae* strain MBG5151; or (2) a recombinant strain of *Saccharomyces cerevisiae* deposited under the Budapest Treaty at the Agricultural Research Service Patent Culture Collection (NRRL) having deposit accession no. NRRL Y-68015 (*Saccharomyces cerevisiae* strain MBG5248.

2. A recombinant *Saccharomyces* yeast strain selected from:

*Saccharomyces cerevisiae* strain deposited under the Budapest Treaty at the Agricultural Research Service Patent Culture Collection (NRRL) having deposit accession no. NRRL Y-67971 (*Saccharomyces cerevisiae* strain MBG5151; and

*Saccharomyces cerevisiae* strain deposited under the Budapest Treaty at the Agricultural Research Service Patent Culture Collection (NRRL) having deposit accession no. NRRL Y-68015 (*Saccharomyces cerevisiae* strain MBG5248.

3. The recombinant *Saccharomyces cerevisiae* strain of claim 2, wherein the strain has one or more of the following properties:

higher ethanol fermentation kinetics compared to *Saccharomyces cerevisiae* CIBTS1260 at 1 g DWC/L, 32° C., pH 5.5;

higher xylose consumption compared to *Saccharomyces cerevisiae* CIBTS1260 after 48 hours fermentation at 1 g DWC/L, 35° C., pH 5.5;

higher glucose consumption compared to *Saccharomyces cerevisiae* CIBTS1260 after 48 hours fermentation at 1 g DWC/L, 35° C., pH 5.5.

4. The recombinant *Saccharomyces cerevisiae* strain of claim 2, wherein the strain has higher ethanol yield compared to *Saccharomyces cerevisiae* CIBTS1260 at 1 g DWC/L, 32° C., pH 5.5 between 10 to 30 hours of fermentation.

5. The recombinant *Saccharomyces cerevisiae* strain of claim 2, wherein the strain has greater than 95% xylose consumption by 48 hours fermentation under the process conditions of 1 g DCW/L, 35° C., pH 5.5.

6. The recombinant *Saccharomyces cerevisiae* strain of claim 2, wherein the strain has greater than 95% glucose consumption by 24 hours fermentation under the process conditions of 1 g DCW/L, 35° C., pH 5.5.

7. The recombinant *Saccharomyces cerevisiae* of claim 2, wherein the strain is capable of providing has more than 30 g/L ethanol after 48 hours fermentation under the process conditions of 1 g DCW/L, 35° C., pH 5.5.

8. The recombinant *Saccharomyces cerevisiae* of claim 2, comprising a heterologous gene encoding a xylose isomerase.

9. The recombinant *Saccharomyces cerevisiae* of claim 2, comprising a heterologous gene encoding a pentose transporter.

10. The recombinant *Saccharomyces cerevisiae* of claim 2, wherein the pentose transporter gene is a GFX gene.

11. The recombinant *Saccharomyces cerevisiae* of claim 2, comprising a heterologous gene encoding a xylulokinase (XKS).

12. The recombinant *Saccharomyces cerevisiae* of claim 2, comprising a heterologous gene encoding a ribulose 5 phosphate 3-epimerase (RPE1), a heterologous gene encoding a ribulose 5 phosphate isomerase (RKI1), or a heterologous gene encoding a transketolase (TKL1) and a heterologous gene encoding a transaldolase (TAL1).

13. A method of producing a derivative of *Saccharomyces cerevisiae* strain MBG5151 (deposited under Accession No. NRRL Y-67971 at the Agricultural Research Service Patent Culture Collection (NRRL)) or *Saccharomyces cerevisiae* strain MBG5248 (deposited under Accession No. NRRL Y-68015 at the Agricultural Research Service Patent Culture Collection (NRRL)) which exhibits the defining characteristics of *Saccharomyces cerevisiae* strain MBG5151 or *Saccharomyces cerevisiae* strain MBG5248, respectively, the method comprising:

(a) providing:

(i) a first yeast strain; and (ii) a second yeast strain, wherein the second yeast strain is *Saccharomyces cerevisiae* strain MBG5151, or *Saccharomyces cerevisiae* strain MBG5248;

(b) culturing the first yeast strain and the second yeast strain under conditions which permit combining of DNA between the first and second yeast strains;

(c) screening or selecting for a derivative of *Saccharomyces cerevisiae* strain MBG5151 or *Saccharomyces cerevisiae* strain MBG5248.

14. The method of claim 13, wherein step (c) comprises screening or selecting for a hybrid strain which exhibits one or more defining characteristic of *Saccharomyces cerevisiae* strain MBG5151 or *Saccharomyces cerevisiae* strain MBG5248.

15. The method of claim 13, comprising the further step of:

(d) repeating steps (a) and (b) with the screened or selected strain from step (c) as the first and/or second strain, until a derivative is obtained which exhibits the defining characteristics of *Saccharomyces cerevisiae* strain MBG5151 or *Saccharomyces cerevisiae* strain MBG5248.

16. The method of claim 13, wherein the culturing step (b) comprises:

(i) sporulating the first yeast strain and the second yeast strain;

(ii) hybridizing germinated spores produced by the first yeast strain with germinated spores produced by the second yeast strain.

17. A method of producing a recombinant derivative of *Saccharomyces cerevisiae* strain MBG5151 (deposited under Accession No. NRRL Y-67971 at the Agricultural Research Service Patent Culture Collection (NRRL)) or *Saccharomyces cerevisiae* strain MBG5248 (deposited under Accession No. NRRL Y-68015 at the Agricultural Research Service Patent Culture Collection (NRRL)), the method comprising:

(a) transforming *Saccharomyces cerevisiae* strain MBG5151 or *Saccharomyces cerevisiae* strain MBG5248 with one or more expression vectors; and (b) isolating the transformed strain.

18. A *Saccharomyces cerevisiae* strain produced by the method of claim 17.

19. A method of producing ethanol, comprising incubating a *Saccharomyces cerevisiae* strain of claim 2 with a substrate comprising a fermentable sugar under conditions which permit fermentation of the fermentable sugar to produce ethanol.

20. A composition comprising a *Saccharomyces cerevisiae* strain of claim 2, and one or more naturally occurring and/or non-naturally occurring components.

* * * * *